(12) United States Patent
Jacobson et al.

(10) Patent No.: US 12,054,755 B2
(45) Date of Patent: Aug. 6, 2024

(54) *Streptococcus canis* CAS9 AS A GENOME ENGINEERING PLATFORM WITH NOVEL PAM SPECIFICITY

(71) Applicant: Massachusetts Institute of Technology, Cambridge, MA (US)

(72) Inventors: Joseph M. Jacobson, Newton, MA (US); Noah Michael Jakimo, Boston, MA (US); Pranam Chatterjee, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 17/683,299

(22) Filed: Feb. 28, 2022

(65) Prior Publication Data
US 2023/0028069 A1    Jan. 26, 2023

Related U.S. Application Data

(63) Continuation of application No. 16/136,238, filed on Sep. 19, 2018, now abandoned.

(60) Provisional application No. 62/560,630, filed on Sep. 19, 2017.

(51) Int. Cl.
| | |
|---|---|
| *C12N 1/00* | (2006.01) |
| *C12N 9/22* | (2006.01) |
| *C12N 15/09* | (2006.01) |
| *C12N 15/10* | (2006.01) |
| *C12N 15/11* | (2006.01) |
| *C12N 15/66* | (2006.01) |

(52) U.S. Cl.
CPC .................. *C12N 9/22* (2013.01); *C12N 1/00* (2013.01); *C12N 15/09* (2013.01); *C12N 15/102* (2013.01); *C12N 15/11* (2013.01); *C12N 15/66* (2013.01); *C12N 2310/20* (2017.05)

(58) Field of Classification Search
None
See application file for complete search history.

(56) References Cited

FOREIGN PATENT DOCUMENTS

| WO | WO 2013/176772 | * | 11/2013 |
| WO | WO 2013/176772 A1 | * | 11/2013 |

OTHER PUBLICATIONS

Chatterjee et al., "MinimalPAMspecificityofahighlysimilar SpCas9 ortholog", Science Advances, 2018; 4:eaau0766. 10 pages.*

* cited by examiner

*Primary Examiner* — Suzanne M Noakes
(74) *Attorney, Agent, or Firm* — Norma E. Henderson

(57) ABSTRACT

A *Streptococcus canis* Cas9 (ScCas9) ortholog and its engineered variants, possessing novel PAM specificity, is an addition to the family of CRISPR-Cas9 systems. ScCas9 endonuclease is used in complex with guide RNA, consisting of identical non-target-specific sequence to that of the guide RNA SpCas9, for specific recognition and activity on a DNA target immediately upstream of either an "NNGT" or "NNNGT" PAM sequence. A novel DNA-interacting loop domain within ScCas9, and other Cas9 orthologs, such as those from *Streptococcus gordonii* and *Streptococcus angionosis* facilitates a divergent PAM sequence from the "NGG" PAM of SpCas9.

9 Claims, 15 Drawing Sheets

Specification includes a Sequence Listing.

Fig. 1

SEQUENCE LISTING

```
<160> NUMBER OF SEQ ID NOS: 15

<210> SEQ ID NO 1
<211> LENGTH: 20
<212> TYPE: DNA
<213> ORGANISM: Streptococcus canis

<400> SEQUENCE: 1
ccgctgacaa cattgttggc                                              20

<210> SEQ ID NO 2
<211> LENGTH: 20
<212> TYPE: DNA
<213> ORGANISM: Streptococcus canis

<400> SEQUENCE: 2
tttcaatggt aagatcattc                                              20
```

```
<210> SEQ ID NO 3
<211> LENGTH: 20
<212> TYPE: DNA
<213> ORGANISM: Streptococcus canis

<400> SEQUENCE: 3
gtttacgctc atcagataga                                               20

<210> SEQ ID NO 4
<211> LENGTH: 10
<212> TYPE: PRT
<213> ORGANISM: Streptococcus canis

<400> SEQUENCE: 4

Ile Lys His Arg Lys Arg Thr Thr Lys Leu
1               5                   10

<210> SEQ ID NO 5
<211> LENGTH: 20
<212> TYPE: DNA
<213> ORGANISM: Streptococcus canis

<400> SEQUENCE: 5
cgaaaggttt tgcactcgac                                               20

<210> SEQ ID NO 6
<211> LENGTH: 20
<212> TYPE: DNA
<213> ORGANISM: Streptococcus canis

<400> SEQUENCE: 6
ttctgtagtc gacggtaccg                                               20

<210> SEQ ID NO 7
<211> LENGTH: 1368
<212> TYPE: PRT
<213> ORGANISM: Streptococcus pyogenes

<400> SEQUENCE: 7

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
```

```
            165                 170                 175
Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
            195                 200                 205

Lys Ala Ile Leu Ser Ala Arg Leu Ser Lys Ser Arg Arg Leu Glu Asn
            210                 215                 220

Leu Ile Ala Gln Leu Pro Gly Glu Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
                275                 280                 285

Leu Phe Leu Ala Ala Lys Asn Leu Ser Asp Ala Ile Leu Leu Ser Asp
                290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
                355                 360                 365

Gln Glu Glu Phe Tyr Lys Phe Ile Lys Pro Ile Leu Glu Lys Met Asp
                370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
                435                 440                 445

Pro Tyr Tyr Val Gly Pro Leu Ala Arg Gly Asn Ser Arg Phe Ala Trp
                450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
                515                 520                 525

Tyr Val Thr Glu Gly Met Arg Lys Pro Ala Phe Leu Ser Gly Glu Gln
                530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Ile Glu Cys Phe Asp
                565                 570                 575

Ser Val Glu Ile Ser Gly Val Glu Asp Arg Phe Asn Ala Ser Leu Gly
                580                 585                 590
```

```
Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
        610                 615                 620

Leu Phe Glu Asp Arg Glu Met Ile Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
        690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
        770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
        850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
        930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys  Tyr Pro Lys Leu Glu  Ser Glu Phe
        995                 1000                1005
```

| | | | | | | | | | | |
|---|---|---|---|---|---|---|---|---|---|---|
| Val | Tyr | Gly | Asp | Tyr | Lys | Val | Tyr | Asp | Val | Arg | Lys | Met | Ile | Ala |
| 1010 | | | | | 1015 | | | | | 1020 |

Lys Ser Glu Gln Glu Ile Gly Lys Ala Thr Ala Lys Tyr Phe Phe
1025                     1030                    1035

Tyr Ser Asn Ile Met Asn Phe Phe Lys Thr Glu Ile Thr Leu Ala
1040                     1045                    1050

Asn Gly Glu Ile Arg Lys Arg Pro Leu Ile Glu Thr Asn Gly Glu
1055                     1060                    1065

Thr Gly Glu Ile Val Trp Asp Lys Gly Arg Asp Phe Ala Thr Val
1070                     1075                    1080

Arg Lys Val Leu Ser Met Pro Gln Val Asn Ile Val Lys Lys Thr
1085                     1090                    1095

Glu Val Gln Thr Gly Gly Phe Ser Lys Glu Ser Ile Leu Pro Lys
1100                     1105                    1110

Arg Asn Ser Asp Lys Leu Ile Ala Arg Lys Lys Asp Trp Asp Pro
1115                     1120                    1125

Lys Lys Tyr Gly Gly Phe Asp Ser Pro Thr Val Ala Tyr Ser Val
1130                     1135                    1140

Leu Val Val Ala Lys Val Glu Lys Gly Lys Ser Lys Lys Leu Lys
1145                     1150                    1155

Ser Val Lys Glu Leu Leu Gly Ile Thr Ile Met Glu Arg Ser Ser
1160                     1165                    1170

Phe Glu Lys Asn Pro Ile Asp Phe Leu Glu Ala Lys Gly Tyr Lys
1175                     1180                    1185

Glu Val Lys Lys Asp Leu Ile Ile Lys Leu Pro Lys Tyr Ser Leu
1190                     1195                    1200

Phe Glu Leu Glu Asn Gly Arg Lys Arg Met Leu Ala Ser Ala Gly
1205                     1210                    1215

Glu Leu Gln Lys Gly Asn Glu Leu Ala Leu Pro Ser Lys Tyr Val
1220                     1225                    1230

Asn Phe Leu Tyr Leu Ala Ser His Tyr Glu Lys Leu Lys Gly Ser
1235                     1240                    1245

Pro Glu Asp Asn Glu Gln Lys Gln Leu Phe Val Glu Gln His Lys
1250                     1255                    1260

His Tyr Leu Asp Glu Ile Ile Glu Gln Ile Ser Glu Phe Ser Lys
1265                     1270                    1275

Arg Val Ile Leu Ala Asp Ala Asn Leu Asp Lys Val Leu Ser Ala
1280                     1285                    1290

Tyr Asn Lys His Arg Asp Lys Pro Ile Arg Glu Gln Ala Glu Asn
1295                     1300                    1305

Ile Ile His Leu Phe Thr Leu Thr Asn Leu Gly Ala Pro Ala Ala
1310                     1315                    1320

Phe Lys Tyr Phe Asp Thr Thr Ile Asp Arg Lys Arg Tyr Thr Ser
1325                     1330                    1335

Thr Lys Glu Val Leu Asp Ala Thr Leu Ile His Gln Ser Ile Thr
1340                     1345                    1350

Gly Leu Tyr Glu Thr Arg Ile Asp Leu Ser Gln Leu Gly Gly Asp
1355                     1360                    1365

<210> SEQ ID NO 8
<211> LENGTH: 1375
<212> TYPE: PRT
<213> ORGANISM: Streptococcus canis

<400> SEQUENCE: 8

```
Met Glu Lys Lys Tyr Ser Ile Gly Leu Asp Ile Gly Thr Asn Ser Val
1               5                   10                  15

Gly Trp Ala Val Ile Thr Asp Asp Tyr Lys Val Pro Ser Lys Lys Phe
            20                  25                  30

Lys Val Leu Gly Asn Thr Asn Arg Lys Ser Ile Lys Lys Asn Leu Met
                35                  40                  45

Gly Ala Leu Leu Phe Asp Ser Gly Glu Thr Ala Glu Ala Thr Arg Leu
        50                  55                  60

Lys Arg Thr Ala Arg Arg Arg Tyr Thr Arg Arg Lys Asn Arg Ile Arg
65                  70                  75                  80

Tyr Leu Gln Glu Ile Phe Ala Asn Glu Met Ala Lys Leu Asp Asp Ser
                85                  90                  95

Phe Phe Gln Arg Leu Glu Glu Ser Phe Leu Val Glu Glu Asp Lys Lys
            100                 105                 110

Asn Glu Arg His Pro Ile Phe Gly Asn Leu Ala Asp Glu Val Ala Tyr
            115                 120                 125

His Arg Asn Tyr Pro Thr Ile Tyr His Leu Arg Lys Lys Leu Ala Asp
        130                 135                 140

Ser Pro Glu Lys Ala Asp Leu Arg Leu Ile Tyr Leu Ala Leu Ala His
145                 150                 155                 160

Ile Ile Lys Phe Arg Gly His Phe Leu Ile Glu Gly Lys Leu Asn Ala
                165                 170                 175

Glu Asn Ser Asp Val Ala Lys Leu Phe Tyr Gln Leu Ile Gln Thr Tyr
            180                 185                 190

Asn Gln Leu Phe Glu Glu Ser Pro Leu Asp Glu Ile Glu Val Asp Ala
        195                 200                 205

Lys Gly Ile Leu Ser Ala Arg Leu Ser Lys Ser Lys Arg Leu Glu Lys
210                 215                 220

Leu Ile Ala Val Phe Pro Asn Glu Lys Lys Asn Gly Leu Phe Gly Asn
225                 230                 235                 240

Ile Ile Ala Leu Ala Leu Gly Leu Thr Pro Asn Phe Lys Ser Asn Phe
            245                 250                 255

Asp Leu Thr Glu Asp Ala Lys Leu Gln Leu Ser Lys Asp Thr Tyr Asp
            260                 265                 270

Asp Asp Leu Asp Glu Leu Leu Gly Gln Ile Gly Asp Gln Tyr Ala Asp
        275                 280                 285

Leu Phe Ser Ala Ala Lys Asn Leu Ser Asp Ala Ile Leu Leu Ser Asp
        290                 295                 300

Ile Leu Arg Ser Asn Ser Glu Val Thr Lys Ala Pro Leu Ser Ala Ser
305                 310                 315                 320

Met Val Lys Arg Tyr Asp Glu His His Gln Asp Leu Ala Leu Leu Lys
            325                 330                 335

Thr Leu Val Arg Gln Gln Phe Pro Glu Lys Tyr Ala Glu Ile Phe Lys
            340                 345                 350

Asp Asp Thr Lys Asn Gly Tyr Ala Gly Tyr Val Gly Ile Gly Ile Lys
        355                 360                 365

His Arg Lys Arg Thr Thr Lys Leu Ala Thr Gln Glu Glu Phe Tyr Lys
        370                 375                 380

Phe Ile Lys Pro Ile Leu Glu Lys Met Asp Gly Ala Glu Glu Leu Leu
385                 390                 395                 400

Ala Lys Leu Asn Arg Asp Asp Leu Leu Arg Lys Gln Arg Thr Phe Asp
            405                 410                 415
```

-continued

```
Asn Gly Ser Ile Pro His Gln Ile His Leu Lys Glu Leu His Ala Ile
            420                 425                 430
Leu Arg Arg Gln Glu Glu Phe Tyr Pro Phe Leu Lys Glu Asn Arg Glu
435                 440                 445
Lys Ile Glu Lys Ile Leu Thr Phe Arg Ile Pro Tyr Tyr Val Gly Pro
        450                 455                 460
Leu Ala Arg Gly Asn Ser Arg Phe Ala Trp Leu Thr Arg Lys Ser Glu
465                 470                 475                 480
Glu Ala Ile Thr Pro Trp Asn Phe Glu Glu Val Val Asp Lys Gly Ala
            485                 490                 495
Ser Ala Gln Ser Phe Ile Glu Arg Met Thr Asn Phe Asp Glu Gln Leu
        500                 505                 510
Pro Asn Lys Lys Val Leu Pro Lys His Ser Leu Leu Tyr Glu Tyr Phe
    515                 520                 525
Thr Val Tyr Asn Glu Leu Thr Lys Val Lys Tyr Val Thr Glu Arg Met
    530                 535                 540
Arg Lys Pro Glu Phe Leu Ser Gly Glu Gln Lys Lys Ala Ile Val Asp
545                 550                 555                 560
Leu Leu Phe Lys Thr Asn Arg Lys Val Thr Val Lys Gln Leu Lys Glu
            565                 570                 575
Asp Tyr Phe Lys Lys Ile Glu Cys Phe Asp Ser Val Glu Ile Ile Gly
        580                 585                 590
Val Glu Asp Arg Phe Asn Ala Ser Leu Gly Thr Tyr His Asp Leu Leu
    595                 600                 605
Lys Ile Ile Lys Asp Lys Asp Phe Leu Asp Asn Glu Glu Asn Glu Asp
610                 615                 620
Ile Leu Glu Asp Ile Val Leu Thr Leu Thr Leu Phe Glu Asp Arg Glu
625                 630                 635                 640
Met Ile Glu Glu Arg Leu Lys Thr Tyr Ala His Leu Phe Asp Asp Lys
            645                 650                 655
Val Met Lys Gln Leu Lys Arg Arg His Tyr Thr Gly Trp Gly Arg Leu
        660                 665                 670
Ser Arg Lys Met Ile Asn Gly Ile Arg Asp Lys Gln Ser Gly Lys Thr
    675                 680                 685
Ile Leu Asp Phe Leu Lys Ser Asp Gly Phe Ser Asn Arg Asn Phe Met
    690                 695                 700
Gln Leu Ile His Asp Asp Ser Leu Thr Phe Lys Glu Ile Glu Lys
705                 710                 715                 720
Ala Gln Val Ser Gly Gln Gly Asp Ser Leu His Glu Gln Ile Ala Asp
            725                 730                 735
Leu Ala Gly Ser Pro Ala Ile Lys Lys Gly Ile Leu Gln Thr Val Lys
        740                 745                 750
Ile Val Asp Glu Leu Val Lys Val Met Gly His Lys Pro Glu Asn Ile
    755                 760                 765
Val Ile Glu Met Ala Arg Glu Asn Gln Thr Thr Thr Lys Gly Leu Gln
    770                 775                 780
Gln Ser Arg Glu Arg Lys Lys Arg Ile Glu Glu Gly Ile Lys Glu Leu
785                 790                 795                 800
Glu Ser Gln Ile Leu Lys Glu Asn Pro Val Glu Asn Thr Gln Leu Gln
            805                 810                 815
Asn Glu Lys Leu Tyr Leu Tyr Tyr Leu Gln Asn Gly Arg Asp Met Tyr
        820                 825                 830
Val Asp Gln Glu Leu Asp Ile Asn Arg Leu Ser Asp Tyr Asp Val Asp
```

```
                835                 840                 845
His Ile Val Pro Gln Ser Phe Ile Lys Asp Asp Ser Ile Asp Asn Lys
            850                 855                 860

Val Leu Thr Arg Ser Val Glu Asn Arg Gly Lys Ser Asp Asn Val Pro
865                 870                 875                 880

Ser Glu Glu Val Val Lys Lys Met Lys Asn Tyr Trp Arg Gln Leu Leu
                885                 890                 895

Asn Ala Lys Leu Ile Thr Gln Arg Lys Phe Asp Asn Leu Thr Lys Ala
            900                 905                 910

Glu Arg Gly Gly Leu Ser Glu Ala Asp Lys Ala Gly Phe Ile Lys Arg
        915                 920                 925

Gln Leu Val Glu Thr Arg Gln Ile Thr Lys His Val Ala Arg Ile Leu
930                 935                 940

Asp Ser Arg Met Asn Thr Lys Arg Asp Lys Asn Asp Lys Pro Ile Arg
945                 950                 955                 960

Glu Val Lys Val Ile Thr Leu Lys Ser Lys Leu Val Ser Asp Phe Arg
            965                 970                 975

Lys Asp Phe Gln Leu Tyr Lys Val Arg Asp Ile Asn Asn Tyr His His
            980                 985                 990

Ala His Asp Ala Tyr Leu Asn Ala  Val Val Gly Thr Ala  Leu Ile Lys
        995                 1000                1005

Lys Tyr  Pro Lys Leu Glu Ser  Glu Phe Val Tyr Gly  Asp Tyr Lys
    1010                1015                1020

Val Tyr  Asp Val Arg Lys Met  Ile Ala Lys Ser Glu  Gln Glu Ile
    1025                1030                1035

Gly Lys  Ala Thr Ala Lys Arg  Phe Phe Tyr Ser Asn  Ile Met Asn
    1040                1045                1050

Phe Phe  Lys Thr Glu Val Lys  Leu Ala Asn Gly Glu  Ile Arg Lys
    1055                1060                1065

Arg Pro  Leu Ile Glu Thr Asn  Gly Glu Thr Gly Glu  Val Val Trp
    1070                1075                1080

Asn Lys  Glu Lys Asp Phe Ala  Thr Val Arg Lys Val  Leu Ala Met
    1085                1090                1095

Pro Gln  Val Asn Ile Val Lys  Lys Thr Glu Val Gln  Thr Gly Gly
    1100                1105                1110

Phe Ser  Lys Glu Ser Ile Leu  Ser Lys Arg Glu Ser  Ala Lys Leu
    1115                1120                1125

Ile Pro  Arg Lys Lys Gly Trp  Asp Thr Arg Lys Tyr  Gly Gly Phe
    1130                1135                1140

Gly Ser  Pro Thr Val Ala Tyr  Ser Ile Leu Val Val  Ala Lys Val
    1145                1150                1155

Glu Lys  Gly Lys Ala Lys Lys  Leu Lys Ser Val Lys  Val Leu Val
    1160                1165                1170

Gly Ile  Thr Ile Met Glu Lys  Gly Ser Tyr Glu Lys  Asp Pro Ile
    1175                1180                1185

Gly Phe  Leu Glu Ala Lys Gly  Tyr Lys Asp Ile Lys  Lys Glu Leu
    1190                1195                1200

Ile Phe  Lys Leu Pro Lys Tyr  Ser Leu Phe Glu Leu  Glu Asn Gly
    1205                1210                1215

Arg Arg  Arg Met Leu Ala Ser  Ala Thr Glu Leu Gln  Lys Ala Asn
    1220                1225                1230

Glu Leu  Val Leu Pro Gln His  Leu Val Arg Leu Leu  Tyr Tyr Thr
    1235                1240                1245
```

-continued

```
Gln Asn Ile Ser Ala Thr Gly Ser Asn Leu Gly Tyr Ile
    1250            1255            1260

Glu Gln His Arg Glu Glu Phe Lys Glu Ile Phe Glu Lys Ile Ile
1265                1270                1275

Asp Phe Ser Glu Lys Tyr Ile Leu Lys Asn Lys Val Asn Ser Asn
    1280                1285                1290

Leu Lys Ser Ser Phe Asp Glu Gln Phe Ala Val Ser Asp Ser Ile
    1295                1300                1305

Leu Leu Ser Asn Ser Phe Val Ser Leu Leu Lys Tyr Thr Ser Phe
    1310                1315                1320

Gly Ala Ser Gly Gly Phe Thr Phe Leu Asp Leu Asp Val Lys Gln
    1325                1330                1335

Gly Arg Leu Arg Tyr Gln Thr Val Thr Glu Val Leu Asp Ala Thr
    1340                1345                1350

Leu Ile Tyr Gln Ser Ile Thr Gly Leu Tyr Glu Thr Arg Thr Asp
    1355                1360                1365

Leu Ser Gln Leu Gly Gly Asp
    1370            1375

<210> SEQ ID NO 9
<211> LENGTH: 21
<212> TYPE: DNA
<213> ORGANISM: Homo sapiens

<400> SEQUENCE: 9
gataaatctg gtcttatttc c                                           21

<210> SEQ ID NO 10
<211> LENGTH: 23
<212> TYPE: DNA
<213> ORGANISM: Homo sapiens

<400> SEQUENCE: 10
ggtgagtgag tgtgtgcgtg tgg                                         23

<210> SEQ ID NO 11
<211> LENGTH: 23
<212> TYPE: DNA
<213> ORGANISM: Homo sapiens

<400> SEQUENCE: 11
gctgcagaag ggattccatg agg                                         23

<210> SEQ ID NO 12
<211> LENGTH: 23
<212> TYPE: DNA
<213> ORGANISM: Homo sapiens

<400> SEQUENCE: 12
ggagtgaggg aaacggcccc agg                                         23

<210> SEQ ID NO 13
<211> LENGTH: 23
<212> TYPE: DNA
<213> ORGANISM: Homo sapiens

<400> SEQUENCE: 13
agtgagtgag tgtgtgtgtg ggg                                         23
```

```
<210> SEQ ID NO 14
<211> LENGTH: 23
<212> TYPE: DNA
<213> ORGANISM: Homo sapiens

<400> SEQUENCE: 14
gctgcagaag ggattccaag ggg                                              23

<210> SEQ ID NO 15
<211> LENGTH: 23
<212> TYPE: DNA
<213> ORGANISM: Homo sapiens

<400> SEQUENCE: 15
ggagggaggg aaacagcccc agg                                              23
```

*Streptococcus canis* CAS9 AS A GENOME ENGINEERING PLATFORM WITH NOVEL PAM SPECIFICITY

RELATED APPLICATIONS

This application a continuation of U.S. patent application Ser. No. 16/136,238, filed Sep. 19, 2018, which claims the benefit of U.S. Provisional Application Ser. No. 62/560,630, filed Sep. 19, 2017, the entire disclosure of which is herein incorporated by reference.

FIELD OF THE TECHNOLOGY

The present invention relates to genome editing and, in particular, to a *Streptococcus* Cas9 ortholog having novel PAM specificity, along with variants and uses thereof.

BACKGROUND

The RNA-guided DNA endonucleases (RGENs) of the CRISPR-Cas system, such as Cas9 [M. Jinek, K. Chylinski, I. Fonfara, M. Hauer, J. A. Doudna, et al., "A programmable dual-RNA-guided DNA endonuclease in adaptive bacterial immunity", Science 337, 816-821 (2012)] and Cpf1 (also known as Cas12a) [B. Zetsche, J. S. Gootenberg, O. O. Abudayyeh, I. M. Slaymaker, K. S. Makarova, et al., "Cpf1 is a Single RNA-Guided Endonuclease of a Class 2 CRISPR-Cas System", Cell 163, 759-771 (2015)], have proven to be versatile tools for genome editing and regulation [Sander, J. D. & Joung, J. K., "CRISPR-Cas systems for editing, regulating and targeting genomes", Nature Biotechnology 32, 347-355 (2014); Doudna, J. A. & Charpentier, "E. Genome editing. The new frontier of genome engineering with CRISPR-Cas9", Science 346, 1258096 (2014); L. S. Qi, M. H. Larson, L. A. Gilbert, J. A. Doudna, J. S. Weissman, et al., "Repurposing CRISPR as an RNA-Guided Platform for Sequence-Specific Control of Gene Expression", Cell 152, 1173-1183 (2013)], which have numerous implications in medicine, agriculture, bioenergy, food security, nanotechnology, and beyond [R. Barrangou, P. Horvath, "A decade of discovery: CRISPR functions and applications", Nat. Microbiol. 2, 17092 (2017)].

The range of targetable sequences for CRISPR endonucleases is limited, however, by the need for a specific protospacer adjacent motif (PAM), which is determined by DNA-protein interactions, to immediately follow the DNA sequence specified by the single guide RNA (sgRNA) [Mojica, F. J., et al., "Short motif sequences determine the targets of the prokaryotic CRISPR defense system", Microbiology 155, 733-740 (2009); Shah, S. A., et al., "Protospacer recognition motifs: mixed identities and functional diversity", RNA Biology 10, 891-899 (2013); Jinek, M. et al., "A programmable dual-RNA-guided DNA endonuclease in adaptive bacterial immunity", Science 337, 816-821 (2012); Sternberg, S. H., et al., "DNA interrogation by the CRISPR RNA-guided endonuclease Cas9", Nature 507, 62-67 (2014); Zetsche, B., et al., "Cpf1 is a Single RNA-Guided Endonuclease of a Class 2 CRISPR-Cas System", Cell 163:3, 759-771 (2015); F. Jiang, K. Zhou, L. Ma, S. Gressel, J. A. Doudna, "A Cas9-guide RNA complex preorganized for target DNA recognition", Science 384:6242, 1477-1481 (2015)]. For example, the most widely used variant, *Streptococcus pyogenes* Cas9 (SpCas9), requires an 5'-NGG-3' motif downstream of its RNA-programmed DNA target [Jinek, M. et al., "A programmable dual-RNA-guided DNA endonuclease in adaptive bacterial immunity", Science 337, 816-821 (2012); R. Barrangou, P. Horvath, "A decade of discovery: CRISPR functions and applications", Nat. Microbiol. 2, 17092 (2017); Mojica, F. J., et al., "Short motif sequences determine the targets of the prokaryotic CRISPR defense system", Microbiology 155, 733-740 (2009); Shah, S. A., et al., "Protospacer recognition motifs: mixed identities and functional diversity", RNA Biology 10, 891-899 (2013); Sternberg, S. H., et al., "DNA interrogation by the CRISPR RNA-guided endonuclease Cas9", Nature 507, 62-67 (2014); F. Jiang, K. Zhou, L. Ma, S. Gressel, J. A. Doudna, "A Cas9-guide RNA complex preorganized for target DNA recognition", Science 384:6242, 1477-1481 (2015)].]. In applications that require targeting a precise position along DNA, the current sequence limitation imposed by the small set of known PAM motifs has constrained the impact of synthetic genome engineering efforts [Mojica, F. J., et al., "Short motif sequences determine the targets of the prokaryotic CRISPR defense system", Microbiology 155, 733-740 (2009); Jinek, M. et al., "A programmable dual-RNA-guided DNA endonuclease in adaptive bacterial immunity", Science 337, 816-821 (2012); Zetsche, B., et al., "Cpf1 is a Single RNA-Guided Endonuclease of a Class 2 CRISPR-Cas System", Cell 163:3, 759-771 (2015)].

To relax this constraint, additional Cas9 and Cpf1 variants with distinct PAM motif requirements have been either discovered [F. A. Ran, L. Cong, W. X. Yan, D. A. Scott, J. S. Gootenberg, et al., "In vivo genome editing using *Staphylococcus aureus* Cas9", Nature 520, 186-191 (2015); K. M. Esvelt, P. Mali, J. L. Braff, M. Moosburner, S. J. Yaung, et al., "Orthogonal Cas9 proteins for RNA-guided gene regulation and editing", Nat. Methods 520, 186-191 (2013); E. Kim, T. Koo, S. W. Park, D. Kim, K. Kim, et al., "In vivo genome editing with a small Cas9 orthologue derived from *Campylobacter jejuni*", Nat. Commun. 8, 14500 (2017); H. Hirano, J. S. Gootenberg, T. Horii, O. O. Abudayyeh, M. Kimura, et al., "Structure and Engineering of *Francisella novicida* Cas9", Cell 164, 950-961 (2016); L. B. Harrington, D. Paez-Espino, B. T. Staahl, J. S. Chen, E. Ma, et al., "A thermostable Cas9 with increased lifetime in human plasma", Nat. Commun. 8, 1424 (2017)] or engineered [H. Hirano, J. S. Gootenberg, T. Horii, O. O. Abudayyeh, M. Kimura, et al., "Structure and Engineering of *Francisella novicida* Cas9", Cell 164, 950-961 (2016); L. B. Harrington, D. Paez-Espino, B. T. Staahl, J. S. Chen, E. Ma, et al., "A thermostable Cas9 with increased lifetime in human plasma", Nat. Commun. 8, 1424 (2017); B. P. Kleinstiver, M. S. Prew, S. Q. Tsai, V. V. Topkar, N. T. Nguyen, et al., "Engineered CRISPR-Cas9 nucleases with altered specificities", Nature 523, 481-485 (2015); L. Gao, D. B. T. Cox, W. X. Yan, J. C. Manteiga, M. W Schneider, et al., "Engineered Cpf1 variants with altered specificities", Nat. Biotechnol. 35, 789-792 (2017)] to diversify the range of targetable DNA sequences. In total, these studies have provided only a handful of CRISPR effectors with minimal PAM requirements that enable wide targeting capabilities.

Bioinformatics tools have been utilized to align Clustered Regularly Interspaced Short Palindromic Repeats (CRISPR) cassettes of numerous bacterial species with presumed protospacers in phage or other genomes. This mapping helps to infer and subsequently test PAM sequences of naturally occurring orthologs that possess useful properties, such as decreased size [Ran, F. A. et al., "In vivo genome editing using *Staphylococcus aureus* Cas9", Nature 520, 186-191 (2015); Kim, E. et al., "In vivo genome editing with a small Cas9 orthologue derived from *Campylobacter jejuni*", Nature Communications 8, 14500 (2017)] and thermostability [Harrington, L. et al., "A thermostable Cas9 with increased lifetime in human plasma", bioRxiv (2017)]. However, such analysis does not guarantee efficient activity, and must be followed by assays to validate PAMs. Alternatively, functionally efficient RGENs, such as SpCas9 and Acidaminococcus sp. Cpf1 (AsCpf1), have been utilized as scaffolds for engineering to produce variants with altered PAM specificities [Kleinstiver, B. P. et al., "Engineered CRISPR-Cas9 nucleases with altered specificities", Nature 523, 481-485 (2015); Gao, L., et al., "Engineered Cpf1 variants with altered specificities", Nature Biotechnology 35, 789-792 (2017)], with measured success.

SUMMARY

In one aspect, the invention includes a novel *Streptococcus* Cas9 ortholog and its engineered variants, possessing novel PAM specificity. In another aspect, the invention includes a novel DNA-interacting loop domain within *Streptococcus canis* Cas9 (ScCas9), and other Cas9 orthologs. In a further aspect, the invention includes a method of altering expression of at least one gene product by employing *Streptococcus canis* Cas9 (ScCas9) and other Cas9 orthologs.

In one aspect, the invention is an isolated *Streptococcus canis* Cas9 (ScCas9) protein or transgene expression thereof. The protein may include at least one of the mutations K857A, K1012A, R1069A, N507A, R671A, Q705A, Q935A, N702A, M704A, Q705A, and H708A. In another aspect, the invention is CRISPR-associated DNA endonuclease with PAM interacting domain (PID) amino acid sequences that are at least 80% identical to that of the isolated *Streptococcus canis* Cas9 (ScCas9) protein. The endonuclease may have a PAM specificity of "NNGT" or "NNNGT", may comprise a 10 amino acid loop insertion of "IKHRKRTTKL" [SEQ ID No: 4], or may comprise a 2 amino acid insertion of "KQ" two positions upstream of the first critical arginine (R) residue for PAM binding. In a further aspect, the invention is an isolated, engineered *Streptococcus pyogenes* Cas9 (SpCas9), *Streptococcus thermophilus* Cas9, or Cpf1 protein with a PID as either the PID amino acid composition of the isolated *Streptococcus canis* Cas9 (ScCas9) protein or of CRISPR-associated DNA endonucleases with PAM interacting domain (PID) amino acid sequences that are at least 80% identical to that of the isolated *Streptococcus canis* Cas9 (ScCas9) protein. The protein may include at least one of the amino acid insertions "IKHRKRTTKL" _[SEQ ID No: 4] or a 2 amino acid insertion of "KQ" two positions upstream of the first critical arginine (R) residue for PAM binding. In yet another aspect, the invention is a DNA-interacting loop domain within ScCas9, or a Cas9 ortholog, that facilitates a divergent PAM sequence from the "NGG" PAM of SpCas9. The Cas9 orthologs may comprise *Streptococcus gordonii* or *Streptococcus angionosis*.

In another aspect, the invention is a method for altering expression of at least one gene product by employing *Streptococcus canis* Cas9 (ScCas9) endonucleases in complex with guide RNA, consisting of identical non-target-specific sequence to that of the guide RNA SpCas9, for specific recognition and activity on a DNA target immediately upstream of either an "NNGT" or "NNNGT" PAM sequence. In a further aspect, the invention is a method of altering expression of at least one gene product comprising: introducing into a eukaryotic cell containing and expressing a DNA molecule having a target sequence and encoding the gene product, an engineered, non-naturally occurring CRISPR-Cas system comprising one or more vectors comprising (a) a regulatory element operable in a eukaryotic cell operably linked to at least one nucleotide sequence encoding a CRISPR system guide RNA that hybridizes with the target sequence, and (b) a second regulatory element operable in a eukaryotic cell operably linked to a nucleotide sequence encoding one or more of the proteins in claims 1-10, wherein components (a) and (b) are located on same or different vectors of the system, whereby the guide RNA targets the target sequence and one or more of the proteins in claims 1-10 cleave the DNA molecule, whereby expression of the at least one gene product is altered; and, wherein the proteins and the guide RNA do not naturally occur together.

BRIEF DESCRIPTION OF THE DRAWINGS

Other aspects, advantages and novel features of the invention will become more apparent from the following detailed description of the invention when considered in conjunction with the accompanying drawings, wherein:

FIG. 1 depicts the global pairwise sequence alignment of *Streptococcus pyogenes* Cas9 (SpCas9) [SEQ ID NO: 7] and *Streptococcus canis* Cas9 (ScCas9) [SEQ ID NO: 8].

FIGS. 6-8 demonstrate ScCas PAM specificity in human cells, wherein:

FIG. 6 depicts an example T7E1 analysis of indels produced at VEGFA loci with indicated PAM sequences.

FIG. 7 is a graph depicting a quantitative analysis of T7E1 products.

FIG. 8 is a graph depicting example results from ScCas9-mediated A→G Base Editing.

FIGS. 9-12 demonstrate ScCas9 performance as a genome editing tool, wherein:

FIG. 9 is a graph of results from quantitative analysis of T7E1 products for indicated genomic on-target (VEGFA site 3 [SEQ ID NO: 10], FANCF site 2 [SEQ ID NO: 11], DNMT1 site 4 [SEQ ID NO: 12]) and off-target (VEGFA site 3 [SEQ ID NO: 13], FANCF site 2 [SEQ ID NO: 14], DNMT1 site 4 [SEQ ID NO: 15]) editing.

FIG. 10 is an efficiency heatmap of a mismatch tolerance assay.

FIG. 11 is a dot plot of on-target modification percentages at various gene targets for indicated PAM, as assessed by the T7E1 assay.

FIG. 12 depicts genomic base editing characterization.

FIGS. 13 and 14 depict the relationship of ScCas9 to other *Streptococcus* orthologs, wherein:

FIG. 13 depicts PAM binding enrichment on a 5'-NNNNNNNN-3' PAM library of ScCas9-like SpCas9 variants.

FIG. 14 shows a FACS analysis of binding at an 5'-NGG-3' PAM.

DETAILED DESCRIPTION

Figure 2:
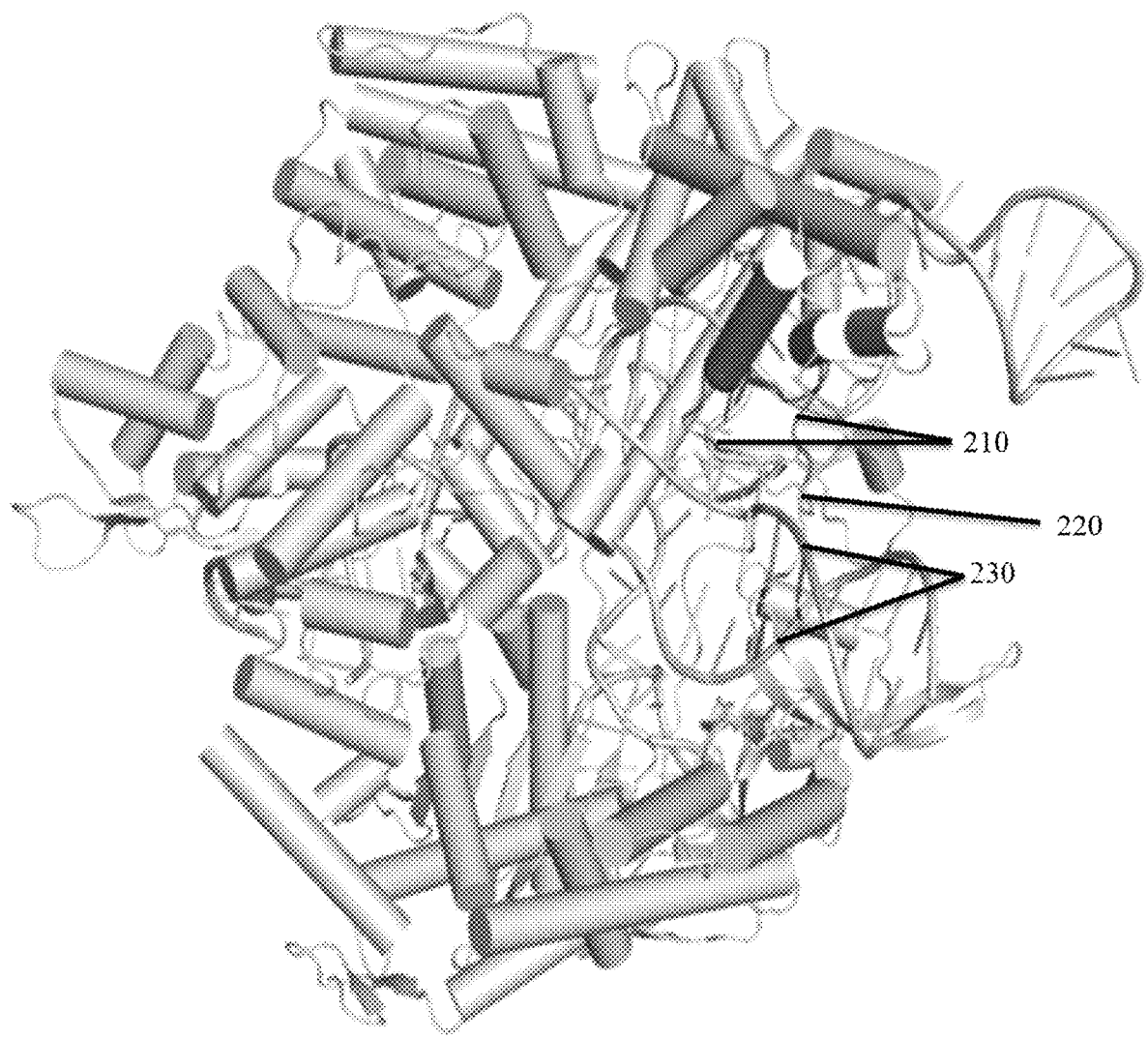
FIG. 2 illustrates the DNA-interacting loop domain within ScCas9, and other Cas9 orthologs, demonstrating that this loop forms expected sequence unspecific contacts with the negatively-charged phosphate backbone of the target DNA strand.

In one aspect, the invention is an addition to the family of CRISPR-Cas9 systems repurposed for genome engineering and regulation applications. Specifically, the invention comprises the usage of *Streptococcus canis* Cas9 (ScCas9) endonuclease in complex with guide RNA, consisting of identical non-target-specific sequence to that of the guide RNA SpCas9, for specific recognition and activity on a DNA target immediately upstream of either an "NNGT" or "NNNGT" PAM sequence, promoting new flexibility in target selection. In a further aspect, the invention is a novel DNA-interacting loop domain within ScCas9, and other Cas9 orthologs, such as those from *Streptococcus gordonii* (Uniprot A0A134D9V8) and *Streptococcus angionosis* (Uniprot F5U0T2), that may facilitate a divergent PAM sequence from the canonical "NGG" PAM of SpCas9.

An orthologous Cas9 protein from *Streptococcus canis*, ScCas9 (UniProt I7QXF2) possesses 89.2% sequence similarity to Sp-Cas9. Despite such homology, ScCas9 prefers a more minimal 5'-NNG-3' PAM. To explain this divergence, two significant insertions were identified within its open reading frame (ORF) that differentiate ScCas9 from SpCas9 and contribute to its PAM-recognition flexibility. ScCas9 can efficiently and accurately edit genomic DNA in mammalian cells.

Identification of SpCas Homologs

While numerous Cas9 homologs have been sequenced, only a handful of *Streptococcus* orthologs have been characterized or functionally validated. To explore this space, all *Streptococcus* Cas9 protein sequences from UniProt [The UniProt Consortium, "UniProt: the universal protein knowledgebase", Nucleic Acids Res. 45, D158-D169 (2017)] were curated, global pairwise alignments using the BLOSUM62 scoring matrix [S. Henikoff, J. G. Henikoff, "Amino acid substitution matrices from protein blocks", Proc. Natl. Acad. Sci. 89, 10915-10919 (1992] were performed, and percent sequence homology to SpCas9 was calculated.

As shown in Table 1, a bioinformatics workflow to identify the PAM specificity of ScCas9 in silico involves the alignment of the spacer sequences within the CRISPR cassette of *Streptococcus canis* with potential protospacers found within the phage and/or other genome databases. As the PAM lies immediately adjacent to the protospacer sequence, these sequences can be conglomerated and weighted based on the number of mismatches to infer bases that are overrepresented at each position [Ran, F. A. et al., "In vivo genome editing using *Staphylococcus aureus* Cas9", Nature 520, 186-191 (2015); Crooks, G. E. et al. "WebLogo: a sequence logo generator", Genome Res. 14, 1188-1190 (2004)].

TABLE 1

| S. canis Spacer (5 to 3') | Photospacer Source | Adjacent Motif (5' to 3') |
| --- | --- | --- |
| CCGCTGACAACATTGTTGGC [SEQ ID No: 1] | Streptococcus pyogenes MGAS2096 (phage protein) | CAGTTAAT |

TABLE 1-continued

| S. canis Spacer (5 to 3') | Photospacer Source | Adjacent Motif (5' to 3') |
| --- | --- | --- |
| TTTCAATGGTAAGATCATTC [SEQ ID No: 2] | Streptococcus phage P9 | ATGTTGAA |
| GTTTACGCTCATCAGATAGA [SEQ ID No: 3] | Streptococcus phage P9 | AAGTCTAA |

Figure 1:
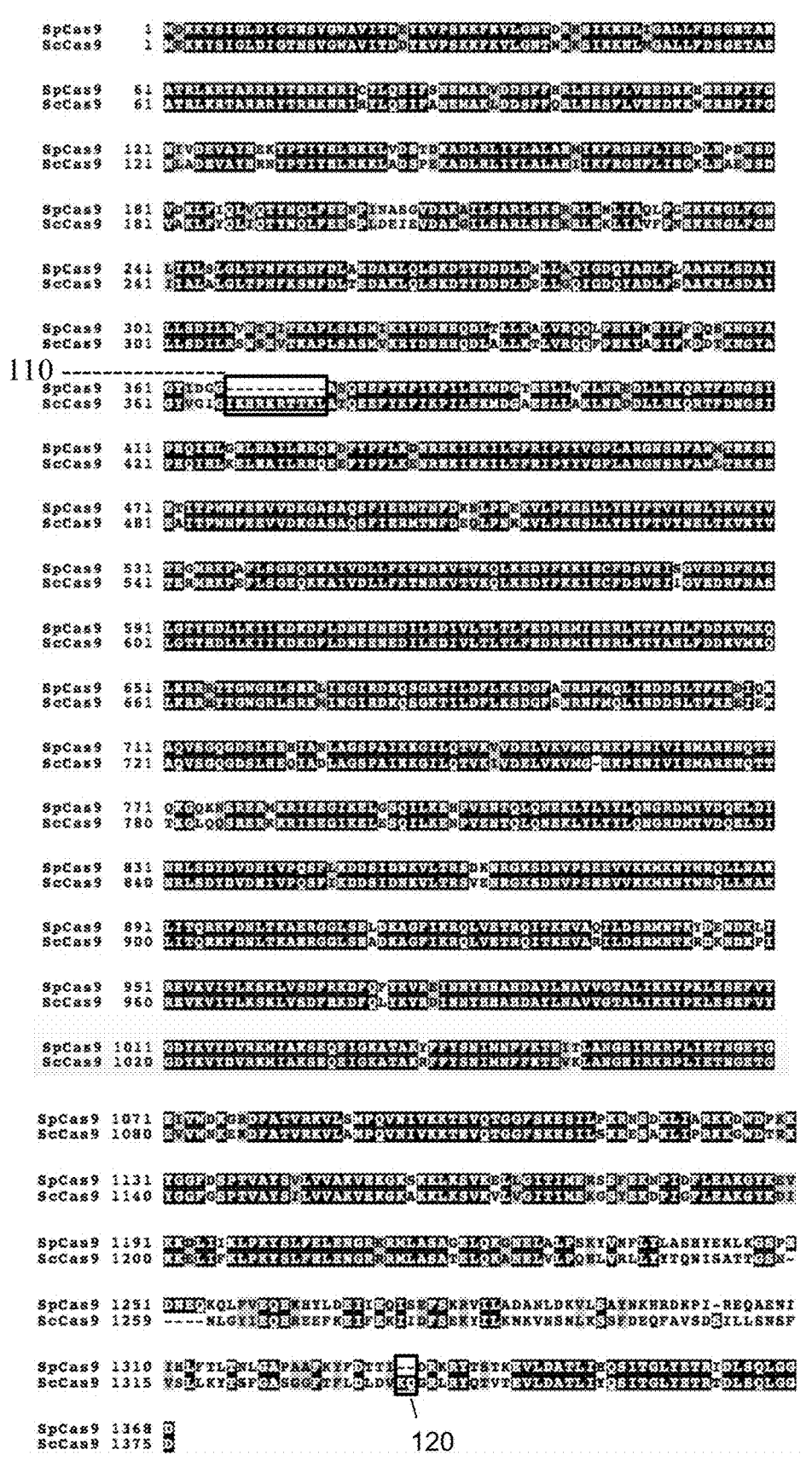

From the calculations, the Cas9 from *Streptococcus canis* (ScCas9) stood out, not only due to its remarkable sequence homology (89.2%) to SpCas9, but also because of a positive-charged insertion of 10 amino acids within the highly-conserved REC3 domain, in positions 367-376. FIG. 1 depicts the global pairwise amino acid sequence alignment of *Streptococcus pyogenes* Cas9 (SpCas9) (Uniprot Q99ZW2) and ScCas9 (Uniprot I7QXF2). Despite sharing 89.2% sequence homology to SpCas9, ScCas9 contains two notable insertions, one positive-charged insertion 110 in the REC domain (367-376) and another KQ insertion 120 in the PAM-interacting domain (1337-1338), as indicated. As seen in FIG. 1, the 10-residue loop, not found in SpCas9, despite otherwise remarkable homology, consists of 8 positively charged amino acids (KHRKRTTK) flanked by two neutral amino acids (I and L).

Exploiting both of these properties, the insertion was modeled within the corresponding domain of PDB 4008 [H. Nishimasu, F. A. Ran, P. D. Hsu, S. Konermann, S. I. Shehata, et al., "Crystal structure of Cas9 in complex with guide RNA and target DNA", Cell 156, 935-949 (2014] and, when viewed in PyMol, it formed a "loop"-like structure, of which several of its positive-charged residues come in close proximity with the target DNA near the PAM. FIG. 2 illustrates the DNA-interacting loop domain within ScCas9, and other Cas9 orthologs, demonstrating that this loop forms expected sequence unspecific contacts with the negatively-charged phosphate backbone of the target DNA strand. Due to the absence of a crystal structure of ScCas9, the in silico insertion of this amino acid motif into PDB 4008, which depicts SpCas9 in complex with guide RNA and target DNA [Nishimasu, H. et al., "Crystal structure of Cas9 in complex with guide RNA and target DNA", Cell 156, 935-949 (2014)], demonstrates that this loop forms expected sequence unspecific contacts with the negatively-charged phosphate backbone of the target DNA strand. As shown in FIG. 2, the novel REC motif is inserted into PDB 4008. The 367-376 insertion demonstrates a loop-like structure 210. Several of its positive-charged residues 220 come in close proximity to the target DNA near the PAM 230. In a preferred embodiment of the invention, the novel loop domain can be inserted into the open reading frame (ORF) of SpCas9, and all characterized Cas9 orthologs, such as *Streptococcus thermophilus* (Uniprot G3ECR1), and other CRISPR endonucleases, such as Cpf1 (Uniprot U2UMQ6 and AOQ7Q2), for the generation of altered PAM specificities through increased protein-DNA interactions.

Figure 3:
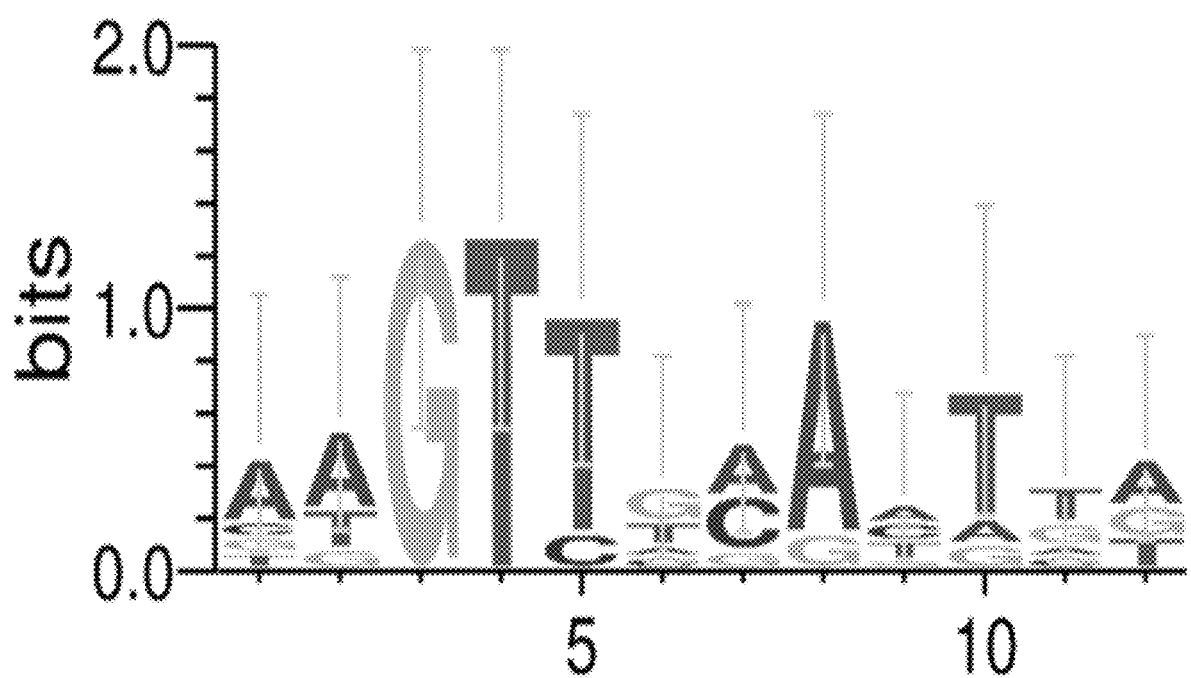
FIG. 3 depicts a WebLogo for sequences found at the 3' end of protospacer targets identified in plasmid and viral genomes using Type II spacer sequences within *Streptococcus canis* as BLAST queries.

An additional insertion of two amino acids (KQ) was identified immediately upstream of the two critical arginine residues necessary for PAM binding [C. Anders, K. Bargsten, M. Jinek, "Structural plasticity of PAM recognition by engineered variants of the RNA-guided endonuclease Cas9", Mol. Cell 61, 895-902 (2016)], in positions 1337-1338 (FIG. 1). It was hypothesized that these insertions may affect the PAM specificity of this enzyme. To support this prediction, the PAM was computationally characterized for ScCas9, by first mapping spacer sequences from the Cas9- associated type II CRISPR loci in the *Streptococcus canis* genome [T. Lef'ebure, V. P. Richards, P. Lang, P. Pavinski-Bitar, M. J. Stanhope, "Gene Repertoire Evolution of *Streptococcus pyogenes* Inferred from Phylogenomic Analysis with *Streptococcus canis* and *Streptococcus dysgalactiae*", PLOS ONE 7, e37607 (2012)] to viral and plasmid genomes using BLAST [S. F. Altschul, W. Gish, W. Miller, E. W. Myers, D. J. Lipman, "Basic Local Alignment Search Tool", Jour. of Mol. Biol. 215, 403-410 (1990)], extracting the sequences 3' to the mapped protospacers, and subsequently a WebLogo [G. E. Crooks, G. Hon, J. M. Chandonia, S. E. Brenner, "WebLogo: A Sequence Logo Generator", Genome Res. 14, 1188-1190 (2004)] representation of the aligned PAM sequences was generated. FIG. 3 is a WebLogo for sequences found at the 3' end of protospacer targets identified in plasmid and viral genomes using Type II spacer sequences within *Streptococcus canis* as BLAST queries.

Analysis suggested an 5'-NNGTT-3' PAM. As FIG. 3 indicates, the sequence logo representing the motifs adjacent to three protospacers complementary to spacers in the *Streptococcus canis* genomic CRISPR cassettes demonstrates a strong preference for guanine (G) at the third position and a thymine (T) at the fourth position. Furthermore, an adenine (A) at position 7 is represented in all three protospacer PAMs, but is a sufficient distance away from the targeting sequence to be critical for Cas9 binding. Intrigued by these novel motifs and motivated by the potentially reduced specificity at position 2 of the PAM sequence, ScCas9 was selected as a candidate for further PAM characterization and engineering.

Determination of PAM Sequences Recognized by ScCas9

Due to the relatively low number of protospacer targets, the PAM binding sequence of ScCas9 was validated utilizing an existent positive selection bacterial screen based on GFP expression conditioned on PAM binding, termed PAM-SCANR [R. T. Leenay, K. R. Maksimchuk, R. A. Slotkowski, R. N. Agrawal, A. A. Gomaa, et al., "Identifying and Visualizing Functional PAM Diversity across CRISPR-Cas Systems", Mol. Cell 62, 137-147 (2016)]. A plasmid library containing the target sequence followed by a randomized 5'-NNNNNNNN-3' (8N) PAM sequence was bound by a nuclease-deficient ScCas9 (and dSpCas9 as a control) and an sgRNA both specific to the target sequence and general for SpCas9 and ScCas9, allowing for the repression of lacI and expression of GFP. Plasmid DNA from FACS-sorted GFP-positive cells and pre-sorted cells were extracted and amplified, and enriched PAM sequences were identified by Sanger sequencing, and visualized utilizing DNA chromatograms. The results provided initial evidence that ScCas9 can bind to the minimal 5'-NNG-3' PAM, distinct to that of SpCas9's 5'-NGG-3'.

Figures 4, 5:
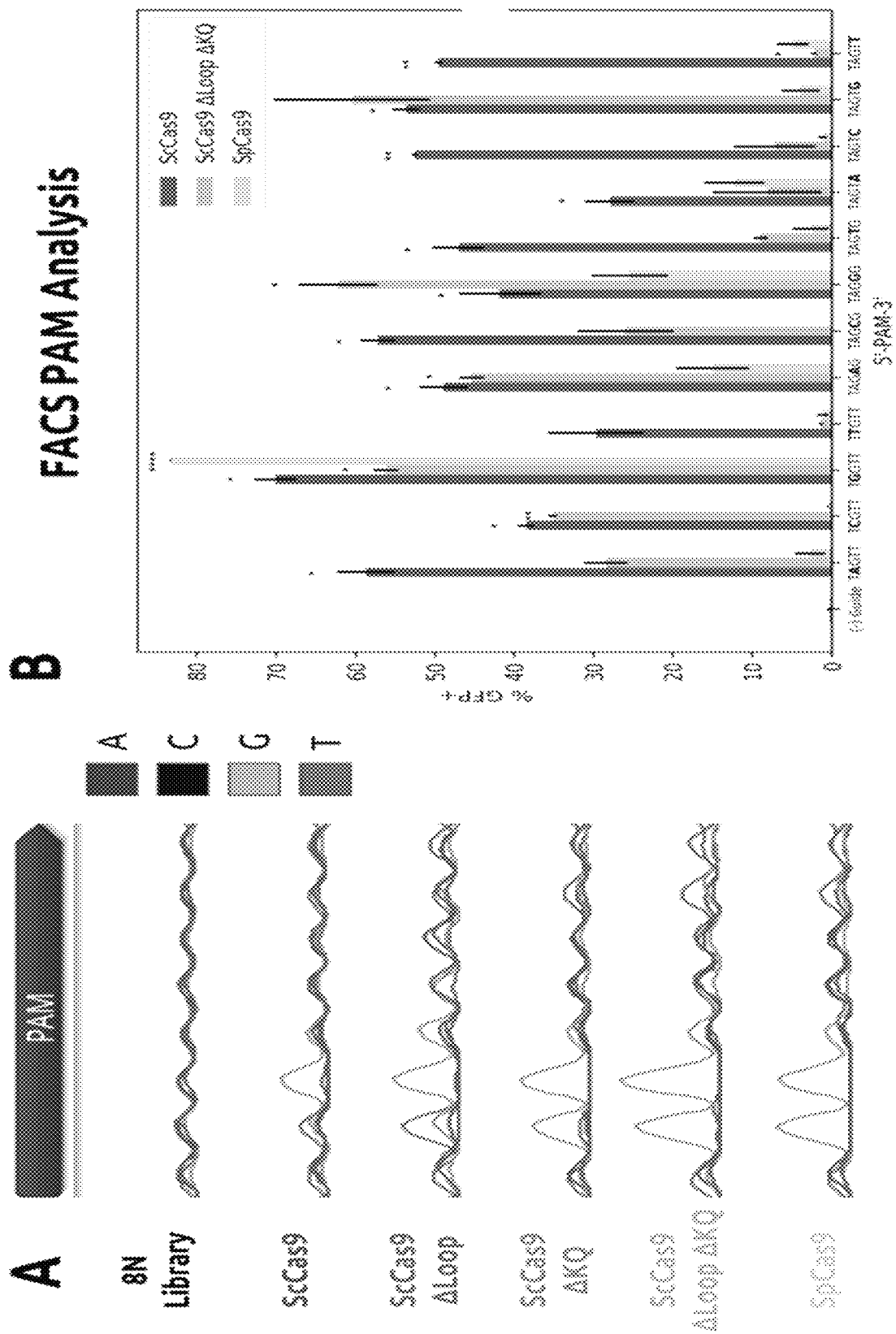
FIG. 4 illustrates PAM determination of engineered ScCas9 variants by showing PAM binding enrichment on a 5'-NNNNNNNN-3' (8N) PAM library.
FIG. 5 is a graph illustrating an examination of PAM preference for ScCas9.

FIGS. 4 and 5 depict aspects of PAM determination of engineered ScCas9 variants. FIG. 4 illustrates PAM binding enrichment on a 5'-NNNNNNNN-3' (8N) PAM library. PAM profiles are represented by Sanger sequencing chromatograms via amplification of PAM region following plasmid extraction of GFP+ *E. coli* cells.

The previously described insertions may contribute to the flexibility permitting ScCas9 to bind to the minimal 5'-NNG-3' PAM, distinct to that of SpCas9's 5'-NGG-3'. ScCas9 was engineered to remove either insertion or both, and subjected these variants to the same screen. Only removing the loop (ScCas9 A367-376 or ScCas9 ΔLoop) extended the PAM of ScCas9 to 5'-NAG-3', with reduced specificity for C and G at position 2, while only removing the KQ insertion (ScCas9 A1337-1338 or ScCas9 AKQ), reverted its specificity to a more 5'-NGG-3'-like PAM, with reduced specificity for A at position 2 (FIG. 4). Finally, the most SpCas9-like variant, where both insertions are removed (ScCas9 A367-376 A1337-1338 or ScCas9 ΔLoop AKQ), expectedly reverted its specificity back to 5'-NGG-3' (FIG. 4). Thus, from a functional perspective, these insertions operate in tandem to reduce the specificity of ScCas9 from the canonical 5'-NGG-3' PAM to a more minimal 5'-NNG-3'.

To confirm the results of the library assay and to rule out limiting downstream requirements, the minimal PAM requirements of ScCas9 were elucidated by utilizing fixed PAM sequences. The PAM library was replaced with individual PAM sequences, which were varied at positions 2, 4, and 5 to test each possible base. The results demonstrate that while ScCas9 exhibits no clear additional base dependence, with activity for all base iterations at each position, ScCas9 ΔLoop AKQ demonstrates significant binding at 5'-NGG-3' PAM sequences and at some, but not all, 5'-NNGNN-3' motifs, indicating an intermediate PAM specificity between that of SpCas9 and ScCas9.

FIG. 5 is a graph illustrating an examination of PAM preference for ScCas9. For individual PAMs, all four bases were iterated at a single position (2, 4, and 5). Each PAM-containing plasmid was electroporated in duplicates, subjected to FACS analysis, and gated for GFP expression. Subsequently, GFP expression levels were averaged. Standard deviation was used to calculate error bars and statistical significance analysis was conducted using a two-tailed Student's t-test as compared to the negative control.

To confirm an expected PAM sequence of "NNGT", a bacterial assay based upon lacI promoter repression of GFP expression, employing 4 nucleotide libraries of PAM sequences upstream of lacI, was utilized [Leenay, R. T. et al., "Identifying and visualizing functional PAM diversity across CRISPR-Cas systems", Mol. Cell 62, 137-147 (2016)]. The library-containing plasmids were co-electroporated with a gRNA plasmid and a nuclease-activity deficient ScCas9 (dScCas9) plasmid, all expressing different antibiotic resistance cassettes. Transformants were plated on triple antibiotic-containing LB agar plates, and GFP positive colonies were subsequently selected and screened.

Sequencing results confirmed that ScCas9 prefers an "NNGT" PAM, but can also tolerate a "NNNGT" PAM, indicating both potential conformational flexibility and strict sequence constraints of the ScCas9 PAM interacting domain (PID). No preference for A was observed at position 7. While various length PAMs with diverse sequences have either been discovered or engineered, this invention, with a PAM specificity of "NNGT" or "NNNGT", different than any known Cas9 variant [Karvelis, T. et al., "Methods for decoding Cas9 protospacer adjacent motif (PAM) sequences: A brief overview", Methods 121-122, 3-6 (2017)] and unable to be engineered from wild-type SpCas9 [Kleinstiver, B. P. et al., "Engineered CRISPR-Cas9 nucleases with altered specificities", Nature 523, 481-485 (2015)] or Cpf1 [Gao, L., et al., "Engineered Cpf1 variants with altered specificities", Nature Biotechnology 35, 789-792 (2017)], augments the list of potential genomic sites that can be targeted by the CRISPR system with high specificity and fidelity in a variety of cell types.

Additionally, there is a two amino acid insertion (KQ) at positions 1328 and 1329, immediately upstream of the two arginine (R) residues critical for PAM binding of Cas9. It is likely that this insertion shifts the length and alters the specificity of the PAM adjacent to the target sequence. A preferred embodiment of this invention enables both the insertion of the KQ motif one amino acid upstream of the first critical arginine residue in SpCas9 to alter its PAM specificity, as well as the removal of the KQ motif in ScCas9 for a similar purpose. Sufficient sequence, and potentially structural, differences from SpCas9 in its PAM interacting domain (PID) further enable exploration of a directed evolution phase space that SpCas9 may not be able to access, through random mutagenesis or rational design, which may also lead to expanded PAM specificities for ScCas9. These engineered PIDs of ScCas9 can be swapped with the PID of SpCas9 to further augment and alter its PAM specificities as well.

Further, due to the high degree of homology between SpCas9 and ScCas9, the propensity to cleave similar, but mismatched, sequences to the intended target is expected to be very similar for both wild-type endonucleases. Much work has been done to characterize and engineer mutations that destabilize strand displacement at mismatched substrates by weakening sequence dependent interactions between Cas9 and DNA (K848A, K1003A, R1060A [Slaymaker, I., et al., "Rationally engineered Cas9 Nucleases with improved specificity", Science 351, 84-88 (2016)] or N497A, R661A, Q695A, Q926A [Kleinstiver, B. P., et al., "High-fidelity CRISPR-Cas9 nucleases with no detectable genome-wide off-target effects", Nature 529, 490-495 (2016)]), and govern mismatch sensing in non-catalytic domains of Cas9 (N692A, M694A, Q695A, H698A) [Chen, J. S. et al. "Enhanced proofreading governs CRISPR-Cas9 targeting accuracy", bioRxiv (2017)]. In a preferred embodiment of this invention, these residue-specific mutations that decrease off-target activity while maintaining robust on-target nuclease activity can be applied to the ORF of ScCas9 to generate a hyper-accurate ScCas9 endonuclease.

For in vitro and in vivo applications, the invention is compatible with existing delivery methods used for other CRISPR-Cas9 systems including, but not limited to, electroporation, lipofection, viral infection, and nanoparticle injection. Embodiments can co-deliver the invention as a coding nucleic acid or protein, along with a gRNA. Components can also be stably expressed in cells.

Assessment of ScCas9 PAM Specificity in Human Cells

The PAM specificity of ScCas9 was compared to SpCas9 in human cells by co-transfecting HEK293T cells with plasmids expressing these variants along with sgRNAs directed to a native genomic locus (VEGFA) with varying PAM sequences (Table S1). Editing efficiency was first tested at a site containing an overlapping PAM (5'-GGGT-3'). After 48 hours post-transfection, gene modification rates, as detected by the T7E1 assay, demonstrated comparable editing activities of SpCas9, ScCas9, and ScCas9 ΔLoop AKQ. Additionally sgRNAs to sites with various non-overlapping 5'-NNGN-3' PAM sequences were constructed. While SpCas9's cleavage activity was impaired at other non-5'-NGG-3' sequences (FIGS. 6 and 7) [P. D. Hsu, D. A. Scott, J. A. Weinstein, F. A. Ran, S. Konermann, et al., "DNA targeting specificities of RNA-guided Cas9 nucleases", Nat. Biotechnol. 31, 827-832 (2013)], ScCas9 maintained comparable activity to that of SpCas9 on its 5'-NGG-3' target across all tested targets with 5'-NNGN-3' PAM sequences.

Figure 6:
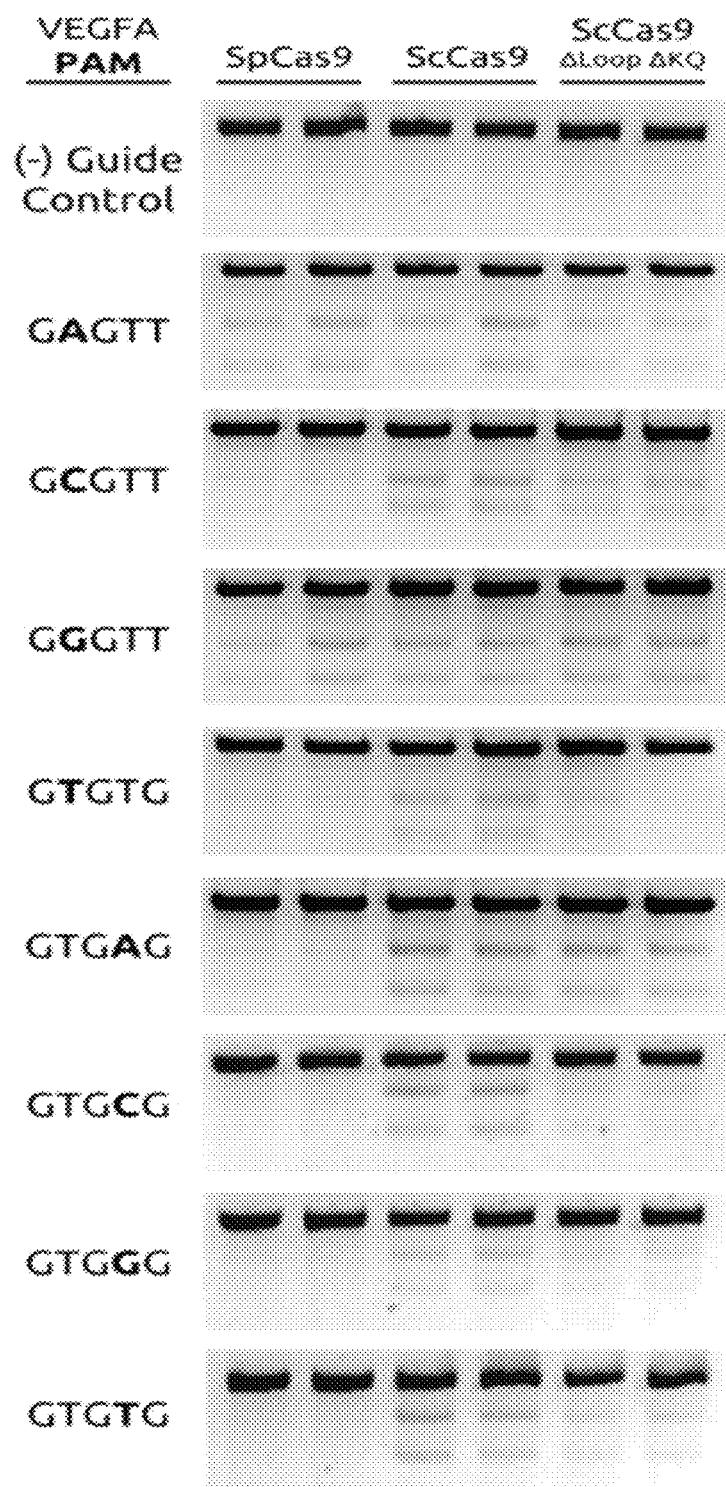
Figure 7:
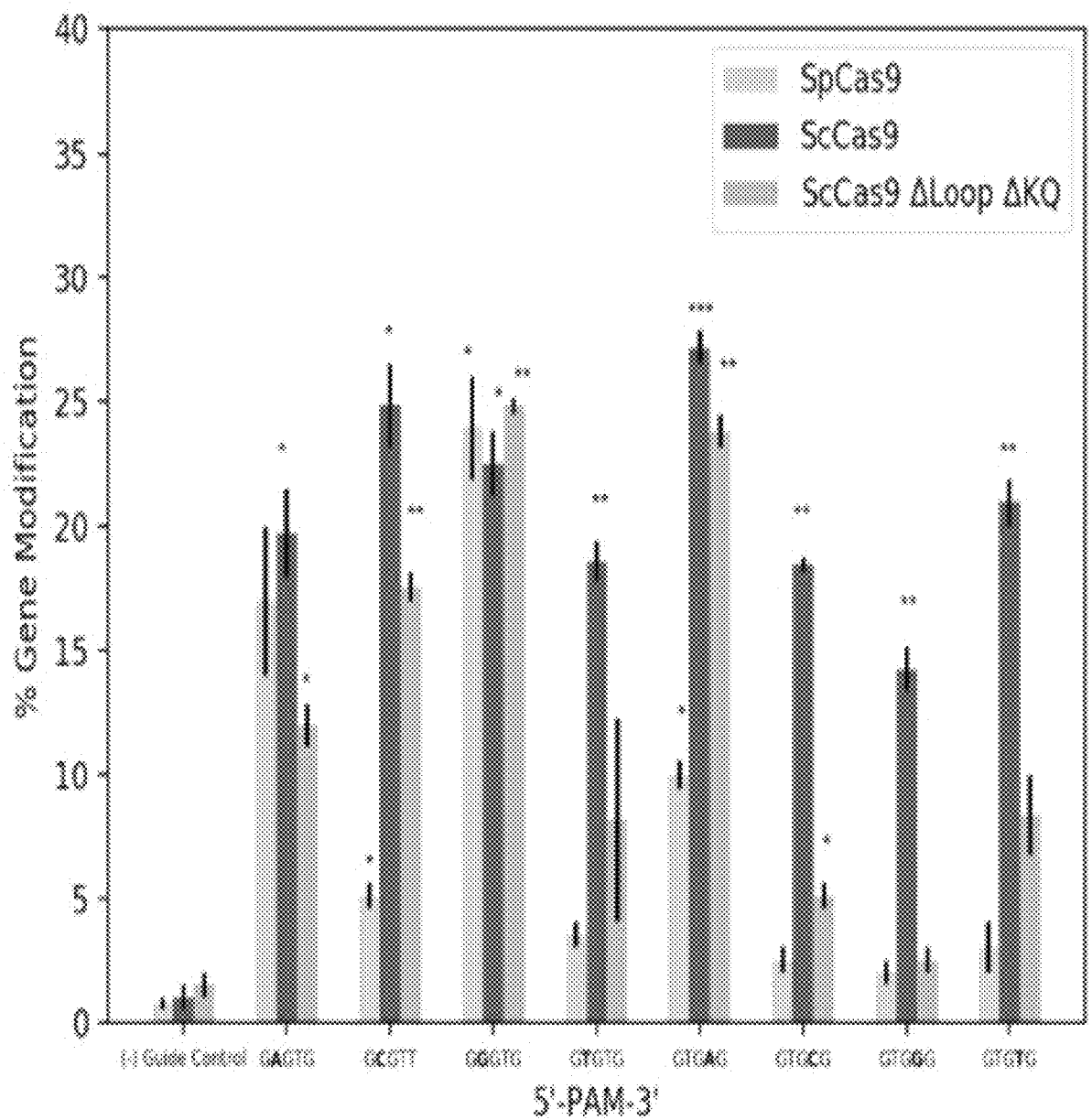

FIG. 6 depicts a T7E1 analysis of indels produced at VEGFA loci with indicated PAM sequences. The Cas9 used is indicated above each lane. All samples were performed in biological duplicates. As a background control, SpCas9, ScCas9, and ScCas9 ΔLoop AKQ were transfected without targeting guide RNA vectors. FIG. 7 is a graph depicting an example quantitative analysis of T7E1 products. Unprocessed gel images were quantified by line scan analysis using Fiji [J. Schindelin, I. Arganda-Carreras, E. Frise, V. Kaynig, M. Longair, et al., "Fiji: an open-source platform for biological-image analysis", Nat. Methods 9, 676-682 (2012], the total intensity of cleaved bands were calculated as a fraction of total product, and percent gene modification was calculated. All samples were performed in duplicates and quantified modification values were averaged. Standard deviation was used to calculate error bars and statistical significance analysis was conducted using a two-tailed Student's t-test as compared to the negative control.

Consistent with the bacterial data, ScCas9 ΔLoop AKQ was able to cleave at the 5'-NGG-3' target, along with significant activity on the 5'-NNGA-3' target, with reduced gene modification levels at all other 5'-NNGN-3' targets (FIGS. 6 and 7). Overall, these results verify that ScCas9 can serve as an effective alternative to SpCas9 for genome editing in mammalian cells, both at overlapping 5'-NGG-3' and more minimal 5'-NNGN-3' PAM sequences.

Figure 8:
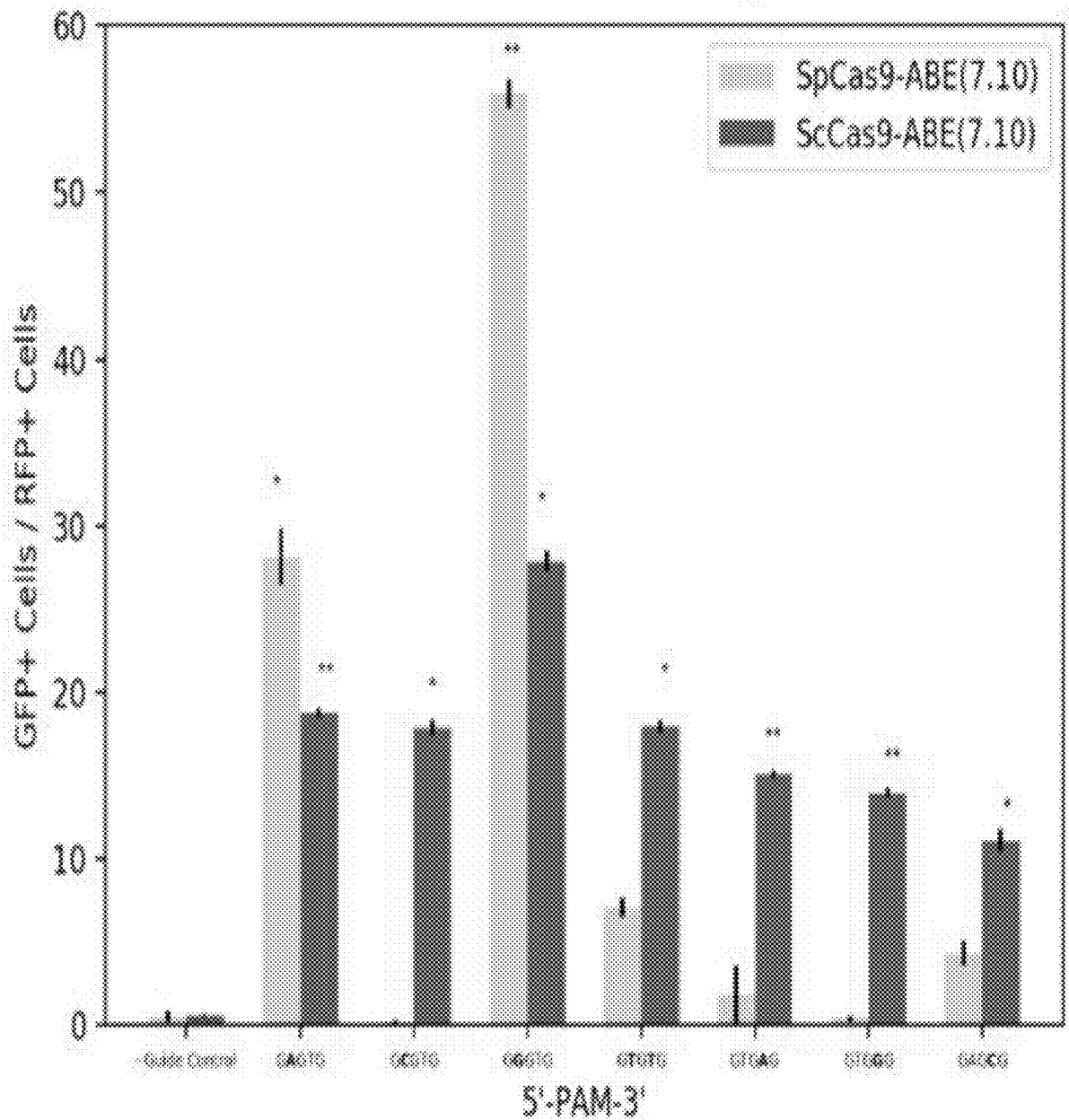

The PAM specificity of ScCas9 base editors was assessed by using a synthetic Traffic Light Reporter (TLR) [M. T. Certo, B. Y. Ryu, J. E. Annis, M. Garibov, J. Jarjour, et al., "Tracking genome engineering outcome at individual DNA breakpoints", Nat. Methods 8, 671-676 (2011)] plasmid, containing an early stop codon upstream of a GFP ORF and downstream of an mCherry ORF. Successful A→G base editing using the ABE (7.10) architecture, as described in Gaudelli, et al. [N. M. Gaudelli, A. C. Komor, H. A. Rees, M. S. Packer, A. H. Badran, et al., "Programmable base editing of A•T to G•C in genomic DNA without DNA cleavage", Nature 551, 464-471 (2017)], converts an early, in-frame TAG stop codon to a TGG tryptophan codon, thus restoring GFP expression. After gating cells based on mCherry expression, significant base editing efficiency was observed at all 5'-NNGN-3' target PAM sequences for ScCas9-ABE (7.10), as compared to the SpCas9-ABE (7.10) architecture, which only demonstrates significant A→G conversion on the standard 5'-NGG-3' and tolerated 5'-NAG-3' motifs in this assay). FIG. 8 is a graph depicting example results from ScCas9-mediated A-G Base Editing. GFP+ cells were calculated as a percentage of mCherry+ cells for indicated PAM sequences using the Traffic Light Reporter [M. T. Certo, B. Y. Ryu, J. E. Annis, M. Garibov, J. Jarjour, et al., "Tracking genome engineering outcome at individual DNA breakpoints", Nat. Methods 8, 671-676 (2011)] with an early stop codon. All samples were performed in duplicates and quantified percentages were averaged. Standard deviation was used to calculate error bars and statistical significance analysis was conducted using a two-tailed Student's t-test.

Off-Target Analysis of ScCas9

The accuracy of this enzyme was evaluated in comparison to SpCas9. Previous genome-wide analysis of SpCas9 targeting accuracy was utilized to select three genomic targets (VEGFA site 3, FANCF site 2, and DNMT1 site 4) that possess multiple off-target sites on which SpCas9 demonstrates activity [S. Q. Tsai, Z. Zheng, N. T. Nguyen, M. Liebers, V. V. Topkar, et al., "GUIDE-seq enables genome-wide profiling of off-target cleavage by CRISPR-Cas nucleases", Nat. Biotechnol. 33, 187-197 (2015)]. Each of these three sites additionally possesses a single off-target that has been particularly difficult to mediate via engineering of high-fidelity Cas9 variants [IM. Slaymaker, L. Gao, B. Zetsche, D. A. Scott, W. X. Yan, et al., "Rationally engineered Cas9 Nucleases with improved specificity", Science 351, 84-88 (2016); B. P. Kleinstiver, V. Pattanayak, M. S. Prew, S. Q. Tsai, N. T. Nguyen, et al., "High-fidelity CRISPR-Cas9 nucleases with no detectable genome-wide off-target effects", Nature 529, 490-495 (2016); J. S. Chen, Y. S. Dagdas, B. P. Kleinstiver, M. M. Welch, A. A. Sousa, et al., "Enhanced proofreading governs CRISPR-Cas9 targeting accuracy", Nature 550, 407-410 (2017)]. ScCas9's activity was analyzed on these off-targets. After co-transfection of sgRNAs to the three aforementioned sites alongside both SpCas9 and ScCas9, genomic DNA flanking both the on-target and difficult off-target sequences was amplified to assess their genome modification activities.

Figure 9:
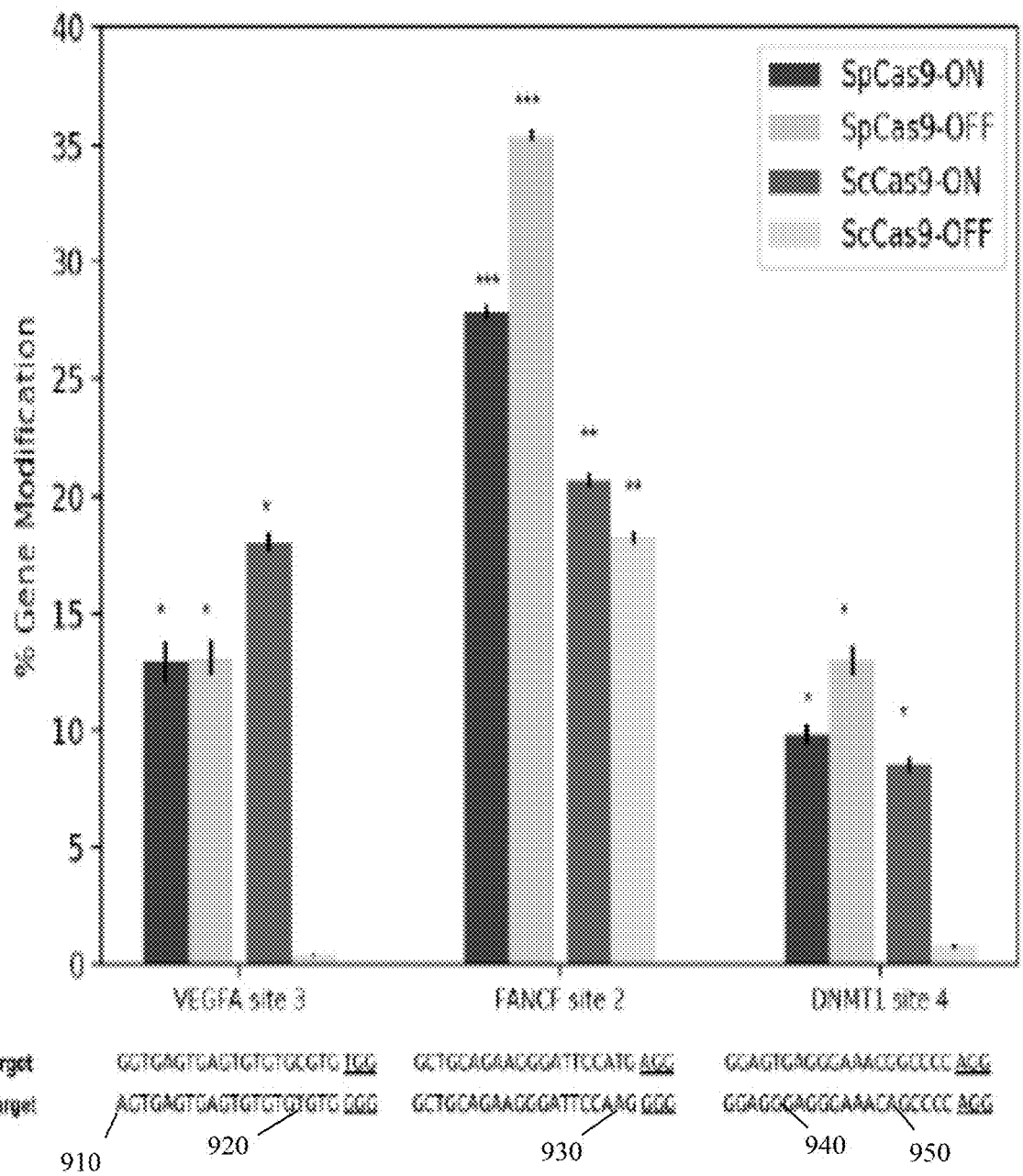

Consistent with previously-reported data [J. S. Chen, Y. S. Dagdas, B. P. Kleinstiver, M. M. Welch, A. A. Sousa, et al., "Enhanced proofreading governs CRISPR-Cas9 targeting accuracy", Nature 550, 407-410 (2017)], SpCas9 demonstrated high off-to-on targeting on all three examined targets. ScCas9 demonstrated comparable on-target activities for the three targets, but exhibited negligible activity on the VEGFA site 3 and DNMT1 site 4 off-targets, and a nearly 1.5-fold decrease in off-to-on target ratio for FANCF site 2, suggesting improved accuracy over SpCas9 on overlapping 5'-NGG-3' targets. FIG. 9 is a graph of results from quantitative analysis of T7E1 products for indicated genomic on- and off-target editing. All samples were performed in duplicates and quantified modification values were averaged. Standard deviation was used to calculate error bars and statistical significance analysis was conducted using a two-tailed Student's t-test as compared to each negative control. Mismatched positions 910, 920, 930, 940, 950 within the spacer sequence are highlighted.

To examine ScCas9's accuracy across its wider PAM targeting range, a mismatch tolerance assay [J. S. Chen, Y. S. Dagdas, B. P. Kleinstiver, M. M. Welch, A. A. Sousa, et al., "Enhanced proofreading governs CRISPR-Cas9 targeting accuracy", Nature 550, 407-410 (2017)] was utilized on target sequences with 5'-NAG-3', 5'-NCG-3', 5'-NGG-3', and 5'-NTG-3' PAMs. sgRNAs containing both single and adjacent double mismatches at every other base along each of the four on-target crRNA sequences were generated, and subsequently the genome modification efficiencies were measured for these mismatched sgRNAs. The results demonstrate that ScCas9 generally tolerates single mismatches better than double mismatches for each analyzed spacer position, and is similarly less likely to tolerate mismatches within the seed region of the crRNA, though with greater sensitivity than SpCas9, as shown in FIG. 10.

Figure 10:
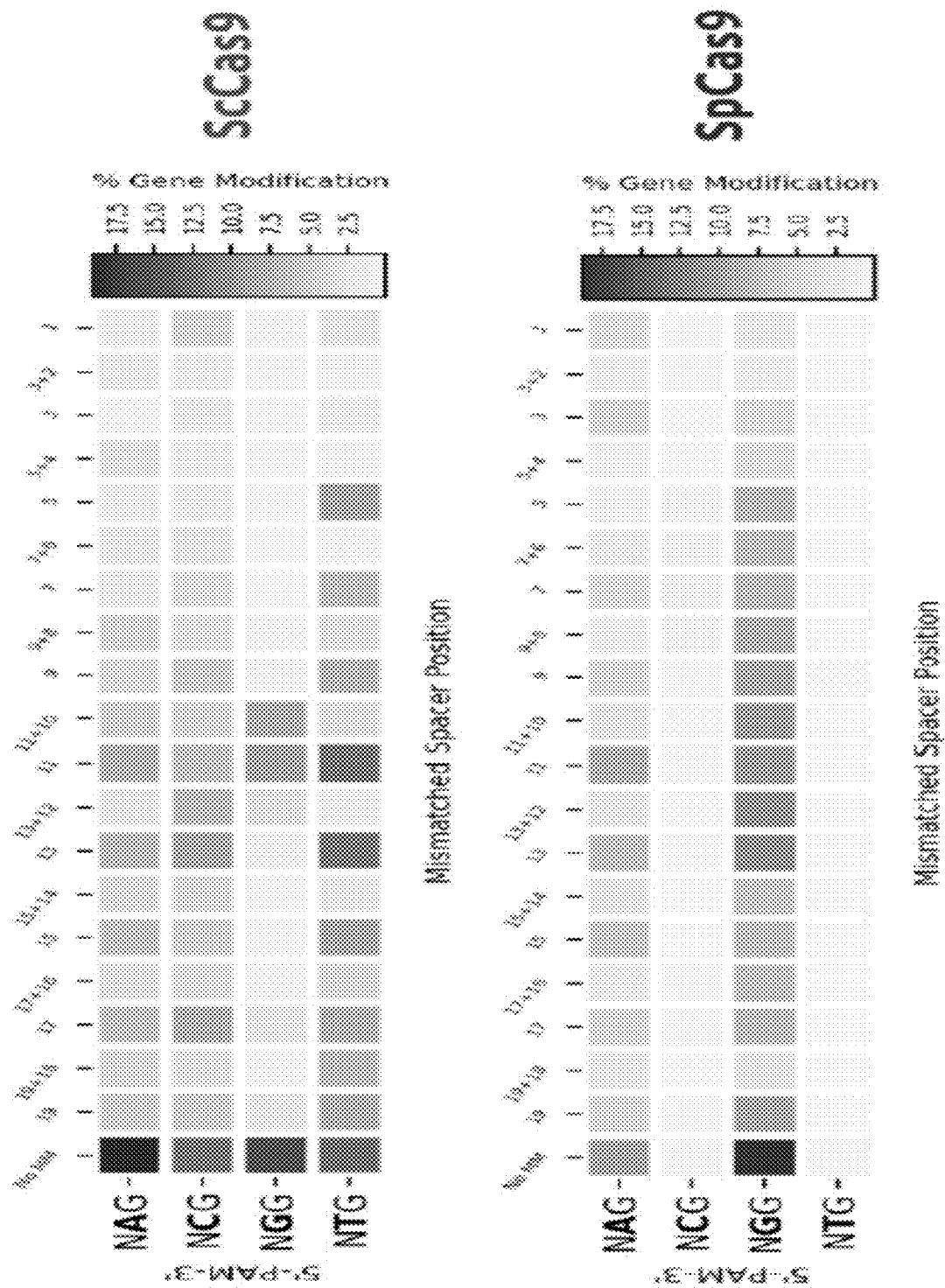

FIG. 10 is an efficiency heatmap of the mismatch tolerance assay. Quantified modification efficiencies, as assessed by the T7E1 assay, are exhibited for each labeled single or double mismatch in the sgRNA sequence for each indicated PAM. Across all of the four PAM targets, ScCas9 does tolerate mismatches within the middle of the crRNA sequence, with highest efficiencies reported for the 5'-NTG-3' target. SpCas9 expectedly demonstrates negligible genome modification activity on the 5'-NCG-3' and 5'-NTG-3' targets, but weakly tolerates single and double mismatches across the entire crRNA sequence, with reduced tolerance in the seed region, for the standard 5'-NGG-3' target, corroborating previous mismatch tolerance studies [J. S. Chen, Y. S. Dagdas, B. P. Kleinstiver, M. M. Welch, A. A. Sousa, et al., "Enhanced proofreading governs CRISPR-Cas9 targeting accuracy", Nature 550, 407-410 (2017)]. Finally, ScCas9 exhibits a similar mismatch tolerance profile to SpCas9 on the 5'-NAG-3' target, albeit with a higher reported on-target efficiency.

ScCas9 Genome Editing Capabilities were evaluated for the ability to modify a variety of gene targets for a handful of different PAM sequences was evaluated. sgRNAs to 24 targets within 9 endogenous genes in HEK293T cells were constructed, and on-target gene modification was evaluated utilizing the T7E1 assay. The results demonstrate that ScCas9 maintains comparable efficiencies to that of SpCas9 on 5'-NGG-3' sequences, as well as on selected 5'-NNG-3' PAM targets, supporting the previous findings (FIG. 7).

Figure 11:
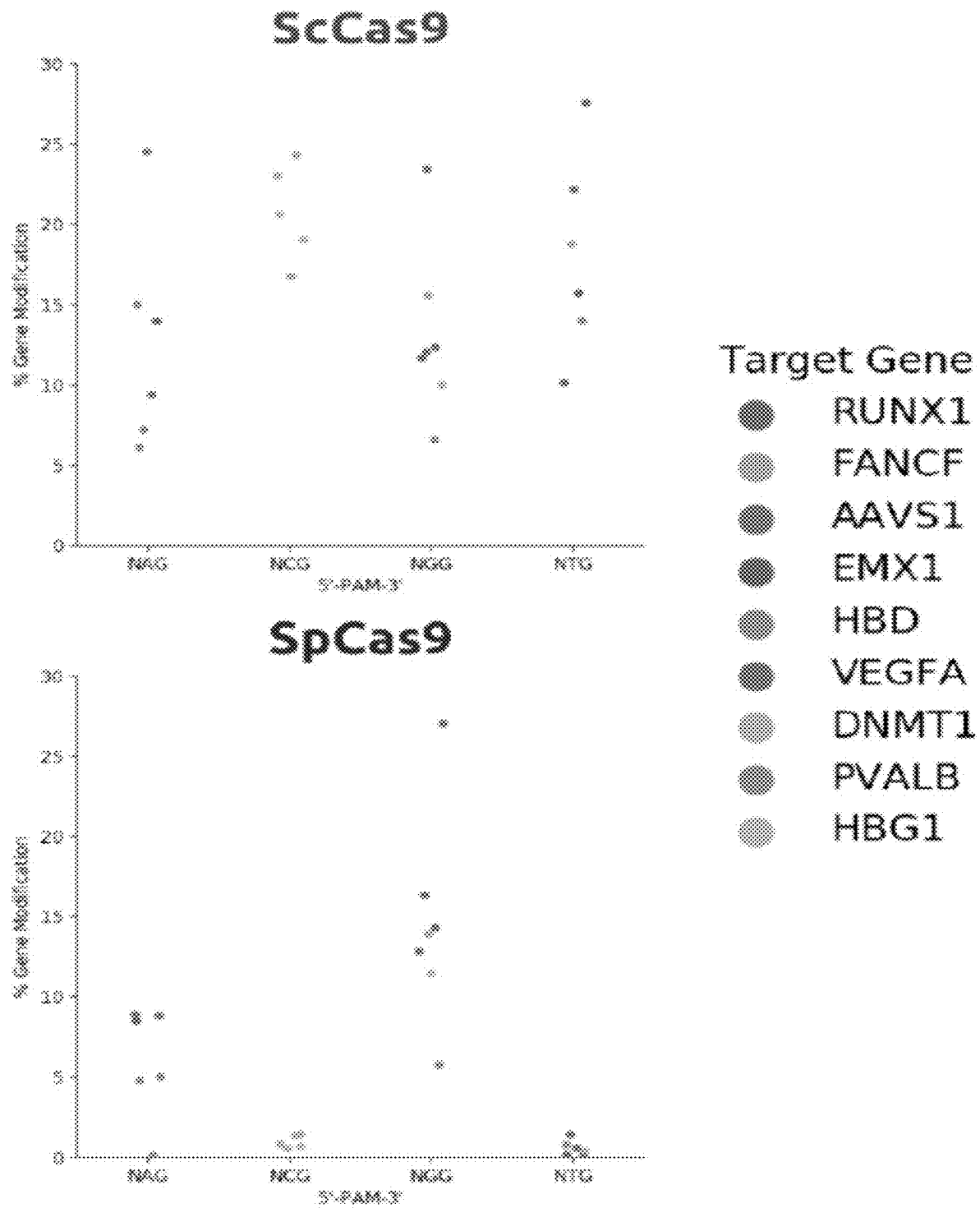

FIG. 11 is a dot plot of on-target modification percentages at various gene targets for indicated PAM as assessed by the T7E1 assay. Duplicate modification percentages were averaged. SpCas9 expectedly performs efficiently on 5'-NGG-3' and weakly on 5'-NAG-3' tar-gets, but demonstrates negligible editing capabilities on 5'-NCG-3' and 5'-NTG-3' PAM sequences, as previously demonstrated. Notably, ScCas9 performed less effectively on selected target sequences in the Hemoglobin subunit delta (HBD) gene, while demonstrating higher efficiencies on 5'-NNG-3' sequences in VEGFA and DNMT1, for example. Such variation in efficiency within each PAM group and across different genes indicates that proper target selection within specified genomic regions is critical for successful ScCas9-mediated gene modification.

The efficacy of ScCas9 integrated within the BE3 [A. C. Komor, Y. B. Kim, M. S. Packer, J. A. Zuris, D. R. Liu, "Programmable editing of a target base in genomic DNA without double-stranded DNA cleavage", Nature 533, 420-424 (2016)] and ABE (7.10) base editing architectures on endogenous genomic loci was subsequently measured. To evaluate the efficiency of base editing activities, a simple, easy-to-use Python program, termed the Base Editing Evaluation Program (BEEP), was developed, which takes as input both a negative control ab1 Sanger sequencing file and the edited sample ab1 file and outputs the efficiency of an indicated base conversion at a specific position (read 5' to 3') along the target sequence.

Figure 12:
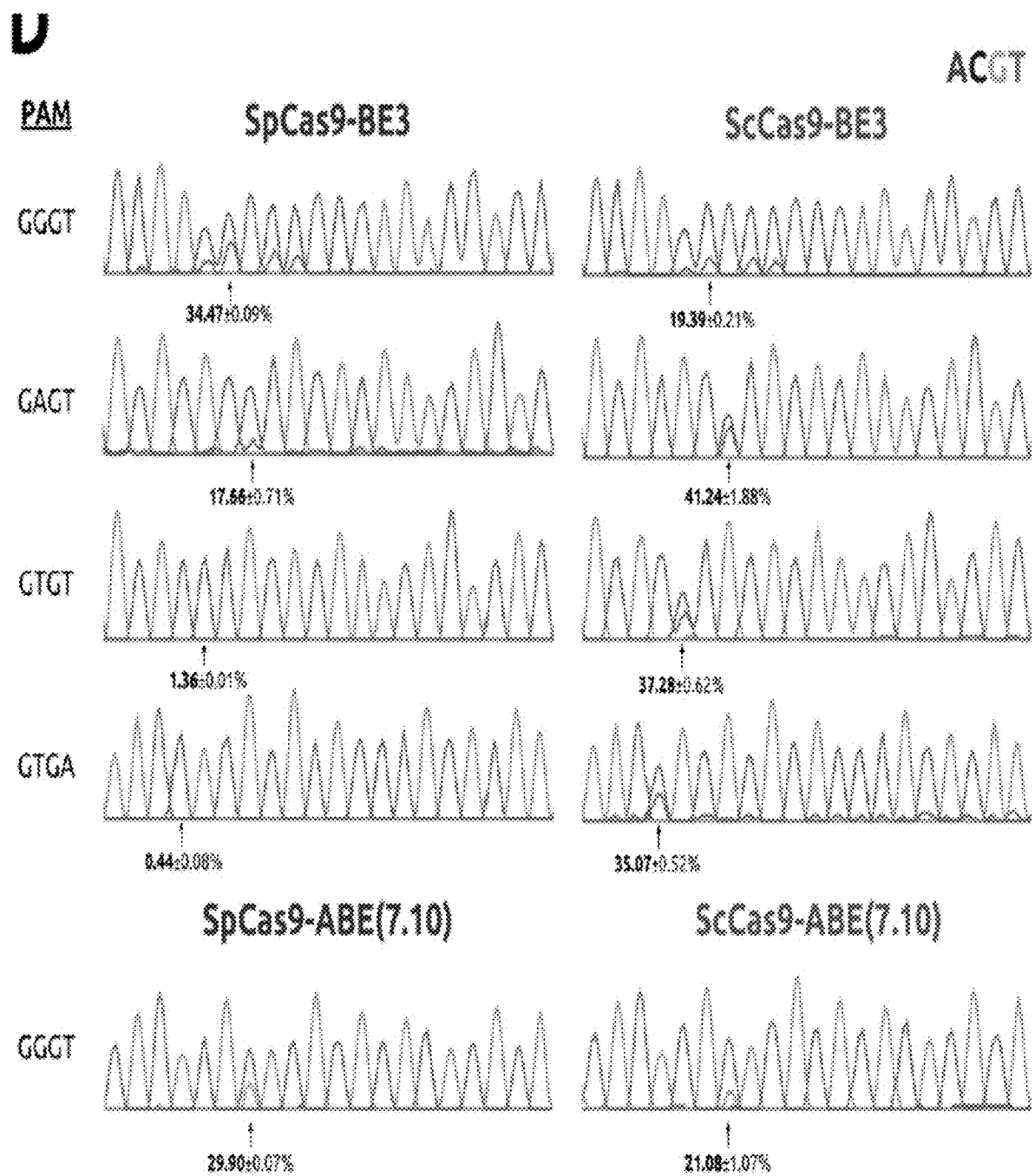

BEEP analysis on ab1 files, following transfection of ScCas9 base editors, genomic amplification, and subsequent Sanger sequencing, demonstrates that ScCas9 is capable of mediating C→T and A→G base conversion at both overlapping 5'-NGG-3' and nonoverlapping 5'-NNG-3' PAM sequences, as shown in FIG. 12, which depicts genomic base editing characterization. For each indicated PAM, a representative Sanger sequencing chromatogram is shown, demonstrating the most efficiently edited base in the target sequence. Percent edited values, as quantified by BEEP in comparison to an unedited negative control, were averaged and standard deviation was subsequently calculated. While ScCas9 base editors perform efficiently on the non-5'-NGG-3' targets, as compared to SpCas9 (FIGS. 8 and 12), ScCas9 is less effective at editing 5'-NGG-3' genomic targets than SpCas9 for both architectures, indicating that further development is necessary for broad usage of ScCas9 base editors.

Figure 13:
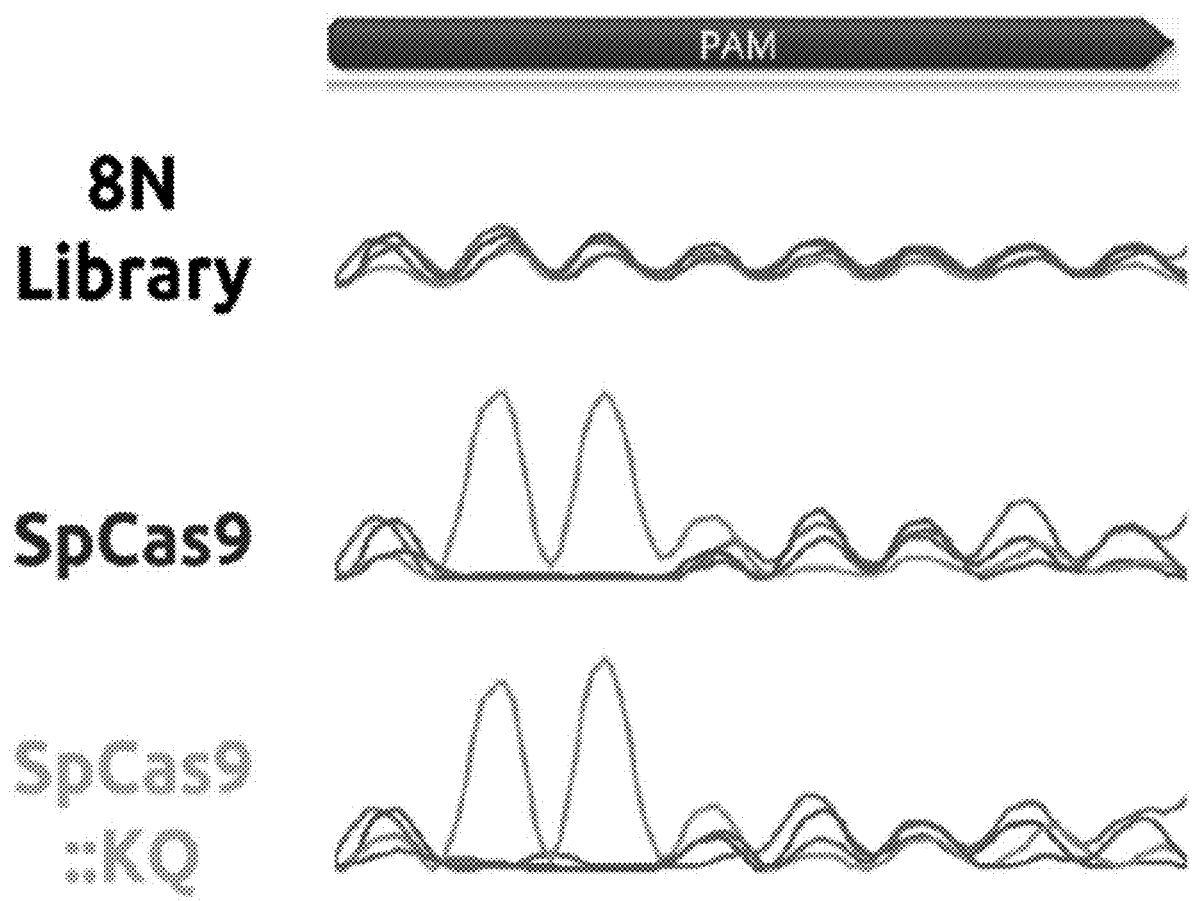

Investigation of Sequence Conservation Between *S. canis* and Other *Streptococcus* Cas9 Orthologs To further investigate the distinguishing motif insertions in ScCas9, the loop (SpCas9::Loop), the KQ motif (SpCas9::KQ), or both (SpCas9::Loop::KQ) were inserted into the Sp-Cas9 ORF and binding on the 8N library was analyzed using PAM-SCANR. Of these variants, only SpCas9::KQ showed target binding affinity in the PAM-SCANR assay. Sequencing on enriched GFP-expressing cells demonstrated an unaffected preference for 5'-NGG-3'. FACS analysis on a fixed 5'-TGG-3' PAM confirmed these binding profiles, with SpCas9::KQ yielding half the fraction of GFP-positive cells compared to SpCas9. This data, in conjunction with the binding profiles of ScCas9 variants, suggests that while these insertions within ScCas9 do distinguish its PAM preference from SpCas9, other sequence features of ScCas9 also contribute to its divergence. FIG. 13 depicts PAM binding enrichment on a 5'-NNNNNNNN-3'

Figure 14:
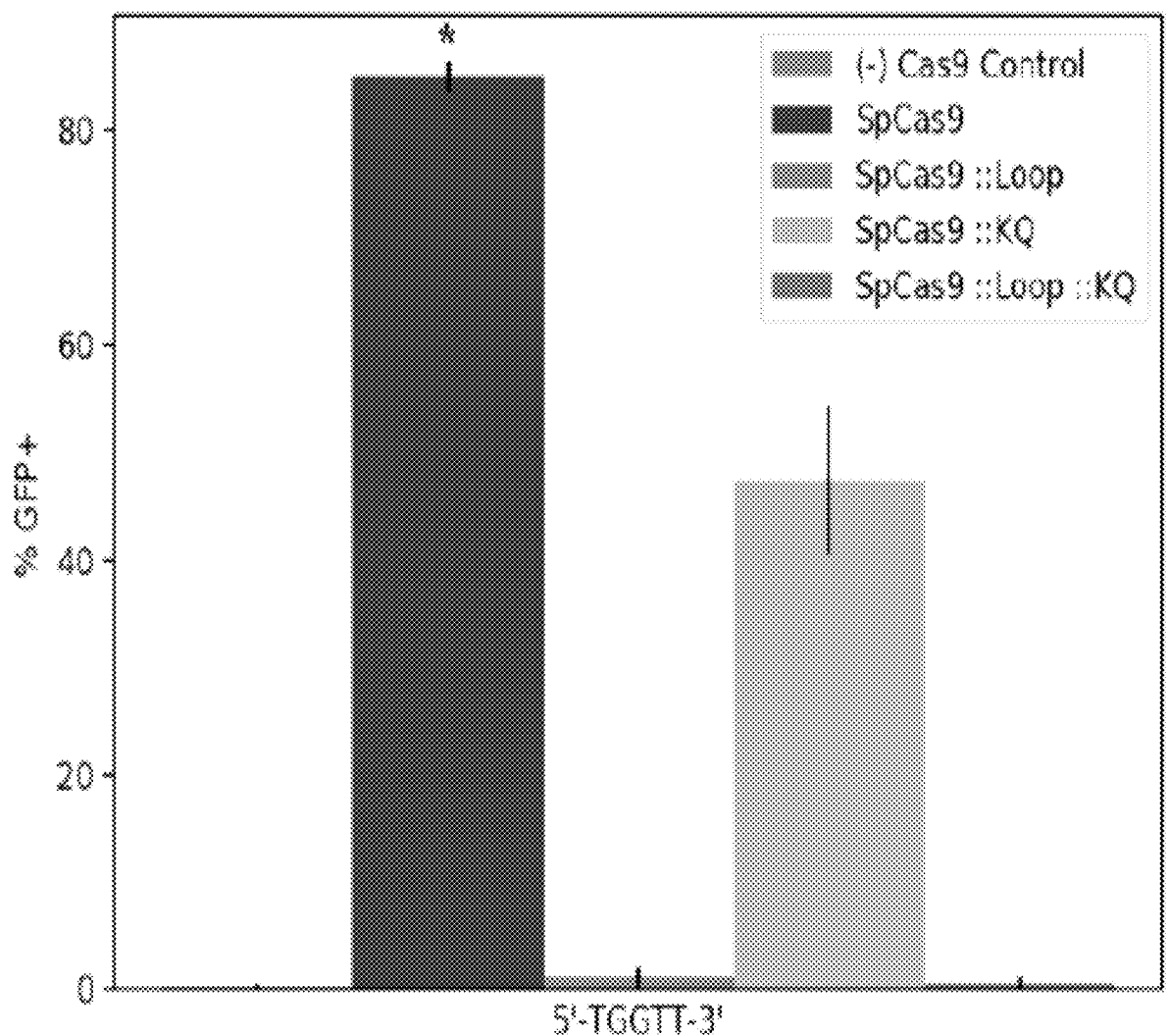

PAM library of ScCas9-like SpCas9 variants. The PAM-SCANR screen (23) was applied to variants of SpCas9 containing either the loop or KQ insertions, or both. SpCas9::Loop and SpCas9::Loop::KQ failed to demonstrate PAM binding and thus GFP expression. FIG. 14 illustrates FACS analysis of binding at an 5'-NGG-3' PAM. All samples were performed in duplicates and averaged. Standard deviation was used to calculate error bars.

S. canis has been reported to infect dogs, cats, cows, and humans, and has been im-plicated as an adjacent evolutionary neighbor of S. pyogenes, as evidenced by various phylogenetic analyses [T. Lef'ebure, V. P. Richards, P. Lang, P. Pavinski-Bitar, M. J. Stanhope, "Gene Repertoire Evolution of Streptococcus pyogenes Inferred from Phylogenomic Analysis with Streptococcus canis and Streptococcus dysgalactiae", PLOS ONE 7, e37607 (2012); 32. V. P. Richards, R. N. Zadoks, P. D. Pavinski Bitar, T. Lefbure, P. Lang, et al., "Genome characterization and population genetic structure of the zoonotic pathogen, Streptococcus canis", BMC Microbiol. 12, 293 (2012); V. P. Richards, S. R. Palmer, P. D. Pavinski Bitar, X. Qin, G. M. Weinstock, et al., "Phylogenomics and the Dynamic Genome Evolution of the Genus Streptococcus", Genome Biol. Evol. 6, 741-753 (2014)]. In addition to sharing common hosts, S. canis CRISPR spacers that map to phage lysogens in S. pyogenes genomes were identified, which suggests they are overlapping viral hosts as well. This close evolutionary relationship has manifested itself in the sequence homology of ScCas9 and SpCas9, amongst other orthologous genes, predicted to be a result of lateral gene transfer (LGT). Nonetheless, from the alignment of SpCas9 and ScCas9, the first 1240 positions score with 93.5% similarity and the last 144 positions score with 52.8%. To account for the exceptional divergence in the PAM-interacting domain (PID) at the C-terminus of ScCas9 as well as the positive-charged inserted loop, focus was placed on alignment of the distinguishing sequences of ScCas9 to other Streptococcus Cas9 orthologs. Notably, the loop motif is present in certain orthologs, such as those from S. gordonii, S. anginosus, and S. intermedius, while the ScCas9 PID is mostly composed of disjoint sequences from other orthologs, such as those from S. phocae, S. varani, and S. equinis. Additional LGT events between these orthologs, as opposed to isolated divergence, more likely explain the differences between ScCas9 and SpCas9. The demonstration that two insertion motifs in ScCas9 alter PAM preferences, yet do not abolish PAM binding when removed, suggests other functional evolutionary intermediates in the formation of effective PAM preferences.

Genus-Wide Prediction of Divergent Streptococcus Cas9 PAMs

Demonstrations of efficient genome editing by Cas9 nucleases with distinct PAM specificity from several Streptococcus species, including S. canis, motivated development of a bioinformatics pipeline for discovering additional Cas9 proteins with novel PAM requirements in the Streptococcus genus. This method was termed the Search for PAMs by ALignment Of Targets (SPAMALOT). Briefly, a 20 nt portion of spacers flanked by known Streptococcus repeat sequences was mapped to candidate protospacers that align with no more than two mismatches in phages associated with the genus [S. A. Shmakov, V. Sitnik, K. S. Makarova, Y. I. Wolf, K. V. Severinov, et al., "The CRISPR Spacer Space Is Dominated by Sequences from Species-Specific Mobilomes", mBio 8, e01397-17 (2017)]. 12 nt protospacer3'-adjacent sequences from each alignment were grouped by genome and CRISPR repeat, and then group WebLogos were generated to compute presumed PAM features.

Figure 15:
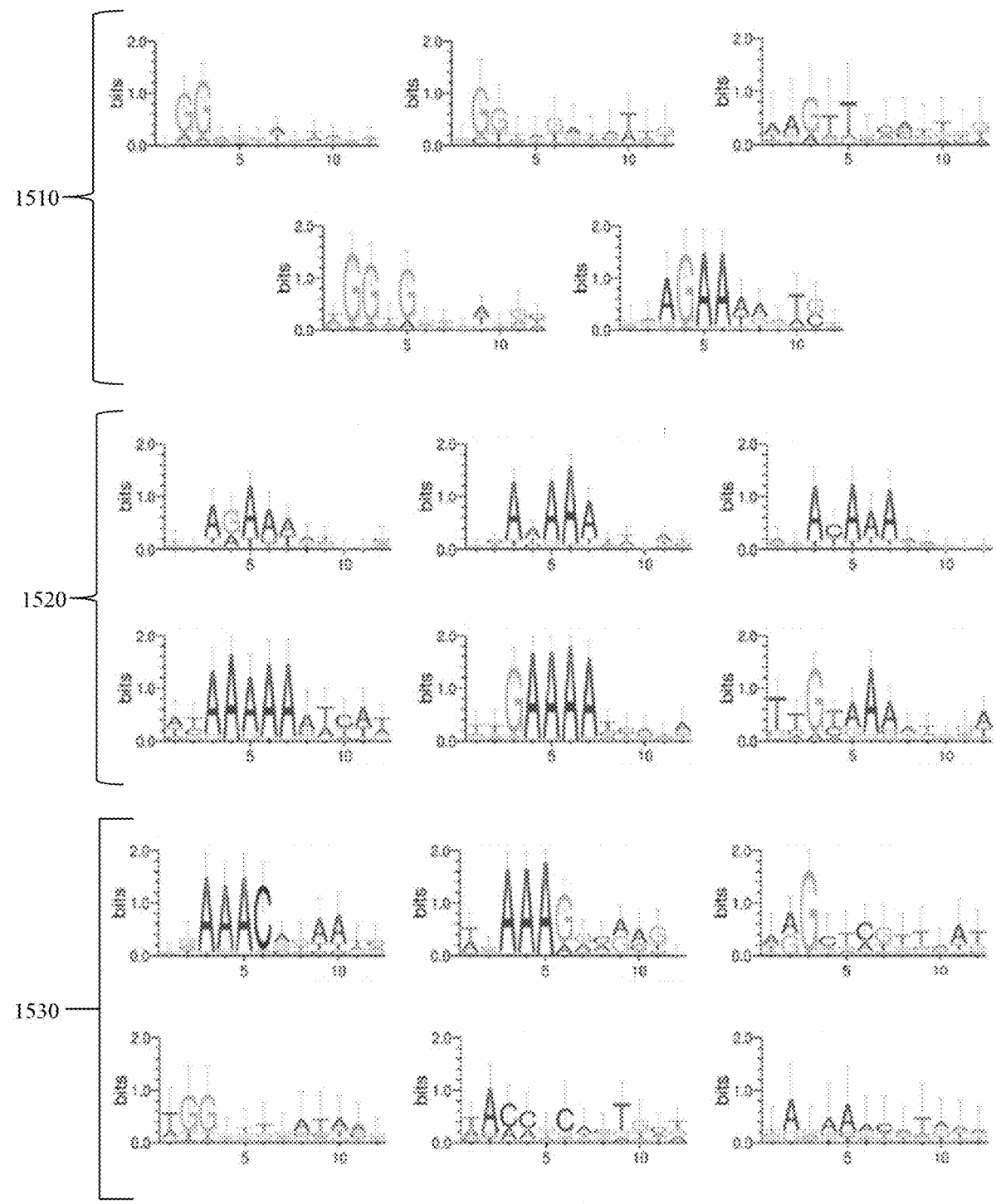
FIG. 15 depicts SPAMALOT PAM Predictions for *Streptococcus* Cas9 Orthologs.

FIG. 15 depicts SPAMALOT PAM Predictions for Streptococcus Cas9 Orthologs. Spacer sequences found within the Type II CRISPR cassettes associated with Cas9 ORFs from specified Streptococcus genomes were aligned to Streptococcus phage genomes to generate spacer-protospacer mappings. WebLogos, labeled with the relevant species, genome, and CRISPR repeat, were generated for sequences found at the 3' end of candidate protospacer targets with no more than two mismatches (2 mm). Shown in FIG. 15 are PAM predictions for experimentally validated Cas9 PAM sequences 1510 in previous studies, novel PAM predictions of alternate S. thermophilus Cas9 orthologs 1520 with putative divergent specificities, and novel PAM predictions of uncharacterized Streptococcus orthologs 1530 with distinct specificities.

FIG. 15 1510 shows that resulting WebLogos accurately reflect the known PAM specificities of Cas9 from S. canis (this work), S. pyogenes, S. thermophilus, and S. mutans [S. H. Sternberg, S. Redding, M. Jinek, E. C. Greene, J. A. Doudna, "DNA interrogation by the CRISPR RNA-guided endonuclease Cas9", Nature 507, 62-67 (2014); M. Muller, C. M. Lee, G. Gasiunas, T. H. Davis, T. J. Cradick, et al., "Streptococcus thermophilus CRISPR-Cas9 Systems Enable Specific Editing of the Human Genome:, Mol. Ther. 24, 636-644 (2016); I. Fonfara, A. L. Rhun, K. Chylinski, K. S. Makarova, A. L. Lcrivain, et al., "Phylogeny of Cas9 determines functional exchangeability of dual-RNA and Cas9 among orthologous type II CRISPR-Cas systems", Nucleic Acids Res. 42, 2577-2590 (2014)]. A notable diversity was identified in the WebLogo plots derived from various S. thermophilus cassettes with common repeat sequences 1520, each of which could originate from any other such S. thermophilus WebLogo upon subtle specificity changes that traverse intermediate WebLogos among them. A similar relationship was observed between two S. oralis WebLogos that also share this repeat, as well as unique putative PAM specificities associated with CRISPR cassettes containing S. mutans-like repeats from the S. oralis, S. equinis, and S. pseudopneumoniae genomes (FIG. 15 1530).

As the growth and development of CRISPR technologies continue, the range of targetable sequences remains limited by the requirement for a PAM sequence flanking a given target site. While significant discovery and engineering efforts have been undertaken to expand this range, there are still only a handful of CRISPR endonucleases with minimal specificity requirements. Here, an analogous platform for genome editing using the Cas9 from Streptococcus canis, a highly-similar SpCas9 ortholog with affinity to minimal 5'-NNG-3' PAM sequences has been developed.

Established PAM engineering methods, such as random mutagenesis and directed evolution, can only generate substitution mutations in protein coding sequences. In fact, another group utilized phage assisted continuous evolution (PACE) [K. M. Esvelt, J. C. Carlson, D. R. Liu, "A system for the continuous directed evolution of biomolecules", Nature 472, 499-503 (2011)] to evolve an SpCas9 variant, xCas9(3.7), with preference for various 5'-NG-3' PAM sequences [J. H. Hu, S. M. Miller, M. H. Geurts, W. Tang, L. Chen, et al., "Evolved Cas9 variants with broad PAM compatibility and high DNA specificity", Nature 556, 5763 (2018)]. An alternative approach consists of inserting or removing motifs with specific properties, which may provide a sequence search space that more common mutagenic techniques cannot directly access. Here, an evolutionary example of this method is demonstrated with ScCas9, whose sequence disparities with SpCas9 include two divergent motifs that contribute to its minimal PAM sequence. Engineered variants lacking these motifs exhibit more stringent PAM specificities in PAM determination assays, and the removal of both motifs reverts its PAM specificity back to a more 5'-NGG-3'-like preference. While minimal inconsistencies in PAM preference between the utilized assays may arise from PAM-dependent allosteric changes that drive DNA cleavage [C. Anders, K. Bargsten, M. Jinek, "Structural plasticity of PAM recognition by engi-neered variants of the RNA-guided endonuclease Cas9", Mol. Cell 61, 895-902 (2016)], the PAM flexibility of ScCas9, as compared to SpCas9, remains consistent in all tested contexts.

To date, there are limited open-source tools or platforms specifically for the prediction of PAM sequences, though prior studies have conducted internal bioinformatics-based characterizations prior to experimental validation. Here, SPAMALOT is established as an accessible resource that is shared with the community for application to CRISPR cassettes from other genera. Future development will include broadening the scope of candidate targets beyond genus-associated phage to capture additional se-quences that could be beneficial targets, such as lysogens in species that host the same phage. It is hoped that this pipeline can be utilized to more efficiently validate and engineer PAM specificities that expand the targeting range of CRISPR, especially for strictly PAM-constrained technologies such as base editing and homology repair induction.

Because ScCas9 does not require any alterations to the sgRNA of SpCas9, and due to its significant sequence homology with SpCas9, identical modifications from previous studies [IM. Slaymaker, L. Gao, B. Zetsche, D. A. Scott, W. X. Yan, et al., "Rationally engineered Cas9 Nucleases with improved specificity", Science 351, 84-88 (2016); B. P. Kleinstiver, V. Pattanayak, M. S. Prew, S. Q. Tsai, N. T. Nguyen, et al., "High-fidelity CRISPR-Cas9 nucleases with no detectable genome-wide off-target effects", Nature 529, 490-495 (2016); J. S. Chen, Y. S. Dagdas, B. P. Kleinstiver, M. M. Welch, A. A. Sousa, et al., "Enhanced proofreading governs CRISPR-Cas9 targeting accuracy", Nature 550, 407-410 (2017)] can be made to increase the accuracy and efficiency of the endonuclease and its variants, although it already demonstrates potential improved on-to-off activity as compared to the standard SpCas9 on 5'-NGG-3' targets. Additionally, while the PAM specificity of ScCas9 on multiple targets in a variety of genome editing contexts has been exhaustively evaluated, the possibility remains that there may exist untested 5'-NNG-3' genomic targets on which ScCas9 does not possess significant activity. Used together with SpCas9 and xCas9(3.7), however, ScCas9 expands the target range of currently-used Cas9 enzymes for genome editing purposes. With further development, this broadened *Streptococcus* Cas9 toolkit, containing both ScCas9 and additional, uncharacterized orthologs with expanded targeting range, will enhance the current set of CRISPR technologies.

Materials and Methods

Identification of Cas9 Homologs and Generation of Plasmids. The UniProt database [The UniProt Consortium, "UniProt: the universal protein knowledgebase", Nucleic Acids Res. 45, D158-D169 (2017)] was mined for all *Streptococcus* Cas9 protein sequences, which were used as inputs to either the BioPython pairwise2 module or Geneious to conduct global pairwise alignments with SpCas9, using the BLOSUM62 scoring matrix [S. Henikoff, J. G. Henikoff, "Amino acid substitution matrices from protein blocks", Proc. Natl. Acad. Sci. 89, 10915-10919 (1992], and subsequently calculate percent homology. The Cas9 from *Streptococcus canis* was codon optimized for *E. Coli*, ordered as multiple gBlocks from Integrated DNA Technologies (IDT), and assembled using Golden Gate Assembly. The pSF-EF1-Alpha-Cas9WT-EMCV-Puro (OG3569) plasmid for human expression of SpCas9 was purchased from Oxford Genetics, and the ORFs of Cas9 variants were individually amplified by PCR to generate 35 bp extensions for subsequent Gibson Assembly into the OG3569 backbone. Engineering of the coding sequence of ScCas9 and SpCas9 for removal or insertion of motifs was conducted using either the Q5 Site-Directed Mutagenesis Kit (NEB) or Gibson Assembly. To generate ScCas9 base editing plasmids, pCMV-ABE (7.10) (Addgene plasmid #102919) and pCMV-BE3 (Addgene plasmid #73021) were received as gifts from David Liu. Similarly, the ORF of the ScCas9 D10A nickase was amplified by PCR to generate 35 bp extensions for subsequent Gibson Assembly into each base editing architecture backbone. sgRNA plasmids were constructed by annealing oligonucleotides coding for crRNA sequences (Table S1) as well as 4 bp overhangs, and subsequently performing a T4 DNA Ligase-mediated ligation reaction into a plasmid backbone immediately downstream of the human U6 promoter sequence. Assembled constructs were transformed into 50 µL NEB Turbo Competent *E. coli* cells, and plated onto LB agar supplemented with the appropriate antibiotic for subsequent sequence verification of colonies and plasmid purification.

PAM-SCANR Assay. Plasmids for the SpCas9 sgRNA and PAM-SCANR genetic circuit, as well as BW25113 ΔlacI cells, were generously provided by the Beisel Lab (North Carolina State University). Plasmid libraries containing the target sequence followed by either a fully-randomized 8-bp 5'-NNNNNNNN-3' library or fixed PAM sequences were constructed by conducting site-directed mutagenesis, utilizing the KLD enzyme mix (NEB) after plasmid amplification, on the PAM-SCANR plasmid flanking the protospacer sequence (5'-CGAAAGGTTTT-GCACTCGAC-3') [SEQ ID No: 5]. Nuclease-deficient mutations (D10A and H850A) were introduced to the ScCas9 variants using Gibson Assembly as previously described. The provided BW25113 cells were made electrocompetent using standard glycerol wash and resuspension protocols. The PAM library and sgRNA plasmids, with resistance to kanamycin (Kan) and carbenicillin (Crb) respectively, were co-electroporated into the electrocompetent cells at 2.4 kV, outgrown, and recovered in Kan+Crb Luria Broth (LB) media overnight. The outgrowth was diluted 1:100, grown to ABS600 of 0.6 in Kan+Crb LB liquid media, and made electrocompetent. Indicated dCas9 plasmids, with resistance to chloramphenicol (Chl), were electroporated in duplicates into the electrocompetent cells harboring both the PAM library and sgRNA plasmids, outgrown, and collected in 5 mL Kan+Crb+Chl LB media. Overnight cultures were diluted to an ABS600 of 0.01 and cultured to an OD600 of 0.2. Cultures were analyzed and sorted on a FACSAria machine (Becton Dickinson). Events were gated based on forward scatter and side scatter and fluorescence was measured in the FITC channel (488 nm laser for excitation, 530/30 filter for detection), with at least 30,000 gated events for data analysis. Sorted GFP-positive cells were grown to sufficient density, and plasmids from the pre-sorted and sorted populations were then isolated, and the region flanking the nucleotide library was PCR amplified and submitted for Sanger sequencing (Genewiz). Bacteria harboring non-library PAM plasmids, performed in duplicates, were analyzed by FACS following electroporation and overnight incubation, and represented as the percent of GFP-positive cells in the population, utilizing standard deviation to calculate error bars. Additional details on the PAM-SCANR assay can be found in Leenay, et al. [R. T. Leenay, K. R. Maksimchuk, R. A. Slotkowski, R. N. Agrawal, A. A. Gomaa, et al., "Identifying and Visualizing Functional PAM Diversity across CRISPR-Cas Systems", Mol. Cell 62, 137-147 (2016].

Figure 16:
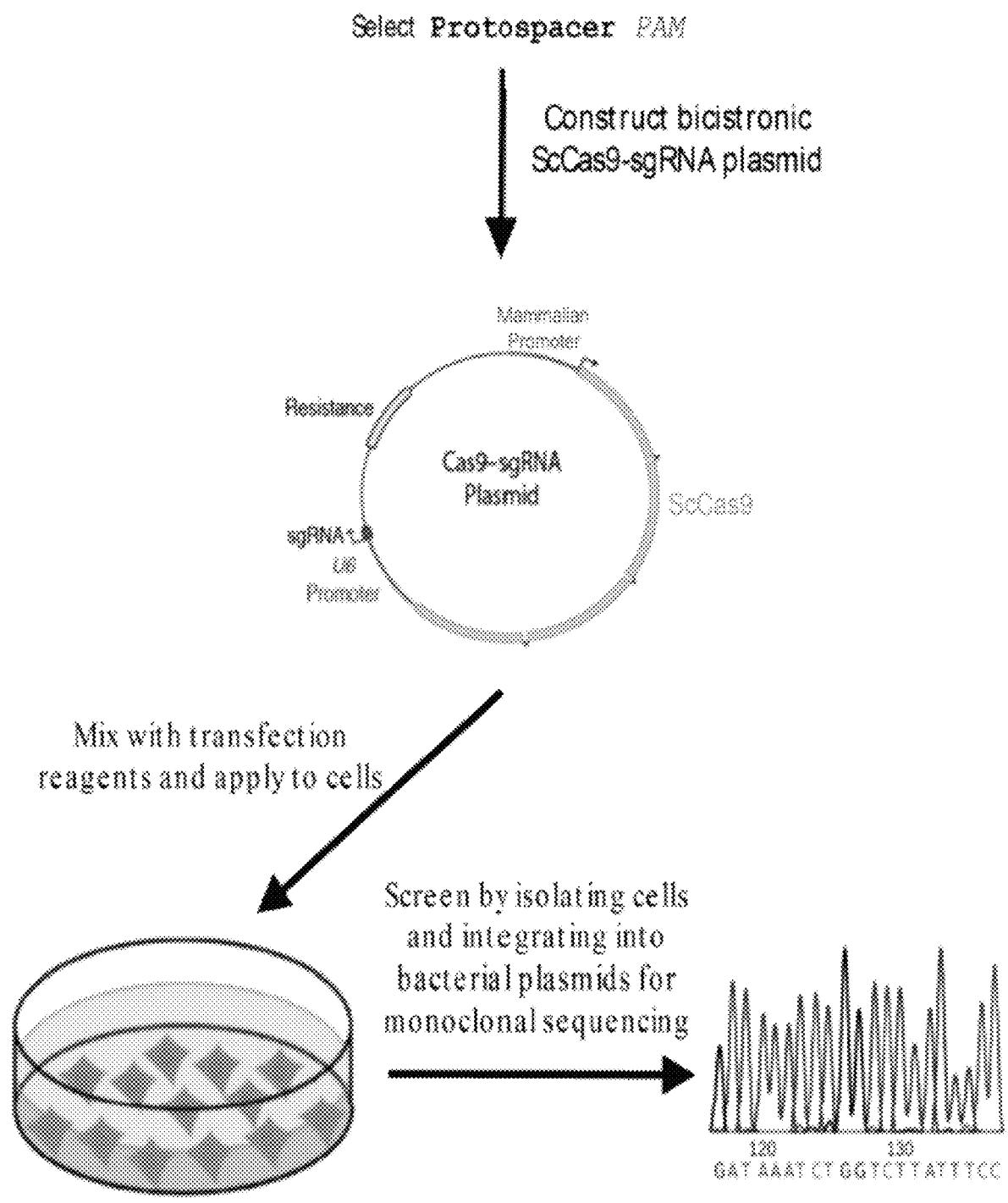
FIG. 16 is a schematic depicting an example workflow to knockout a gene [SEQ ID NO: 9] in cell culture, using ScCas9 according to an aspect of the invention.

Cell Culture and Gene Modification Analysis. FIG. 16 is a schematic depicting an example workflow to knockout a gene in cell culture, using ScCas9 according to an aspect of the invention. As seen in FIG. 16, an example workflow to knockout a gene in cell culture begins with the user's preferred method of selecting a gRNA target adjacent to an ScCas9-specified PAM around a gene of interest from a FASTA sequence file corresponding to this region. Next, a bicistronic vector containing both the gRNA under the control of a U6 promoter and either the coding sequence of the invention or that of its engineered variants, under the control of a mammalian constitutive promoter, is constructed using existing assembly and cloning techniques. Subsequently, the plasmid can be delivered using a standard lipofection reagent (e.g. TransIT-X2 from Mirus Bio LLC) into cell culture. After roughly two days of incubation, individual cells are harvested for genomic extraction to allow an approximately one kilobase (kb) window around the target to be amplified via polymerase chain reaction (PCR). The PCR product is ligated into a bacterial plasmid with a drug selection marker through blunt end cloning and transformed into E. coli. Bacterial colonies are subsequently picked for monoclonal Sanger sequencing and can be carried out by services such as Genewiz.

HEK293T cells were maintained in DMEM supplemented with 100 units/ml penicillin, 100 mg/ml streptomycin, and 10% fetal bovine serum (FBS). sgRNA plasmid (500 ng) and effector (nuclease, BE3, or ABE (7.10)) plasmid (500 ng) were transfected into cells as duplicates (2×105/well in a 24-well plate) with Lipofectamine 2000 (Invitrogen) in Opti-MEM (Gibco). After 48 hours post-transfection, genomic DNA was extracted using QuickExtract Solution (Epicentre), and genomic loci were amplified by PCR utilizing the KAPA HiFi HotStart ReadyMix (Kapa Biosystems). For base editing analysis, amplicons were purified and submitted for Sanger sequencing (Genewiz). For indel analysis, the T7E1 reaction was conducted according to the manufacturer's instructions and equal volumes of products were analyzed on a 2% agarose gel stained with SYBR Safe (Thermo Fisher Scientific). Unprocessed gel image files were analyzed in Fiji [J. Schindelin, I. Arganda-Carreras, E. Frise, V. Kaynig, M. Longair, et al., "Fiji: an open-source platform for biological-image analysis. Nat. Methods 9, 676-682 (2012)]. The cleaved bands of interest were isolated using the rectangle tool, and the areas under the corresponding peaks were measured and calculated as the fraction cleaved of the total product. Percent gene modification was calculated as follows [D. Y. Guschin, A. J. Waite, G. E. Katibah, J. C. Miller, M. C. Holmes, et al., "A Rapid and General Assay for Monitoring Endogenous Gene Modification", Methods Mol. Biol. 649, 247-256 (2010]:

$$\% \text{ gene modification} = 100 \times \left(1 - (1 - \text{fraction cleaved})^{\frac{1}{2}}\right)$$

All samples were performed in duplicates and percent gene modifications were averaged. Standard deviation was used to calculate error bars.

Base editing analysis with Traffic Light Reporter. HEK293T cells were maintained as previously described, and transfected with the corresponding sgRNA plasmids (333 ng), ABE7.10 plasmids (333 ng), and synthetically constructed TLR plasmids (333 ng) into cells as duplicates (2×105/well in a 24-well plate) with Lipofectamine 2000 (Invitrogen) in Opti-MEM (Gibco). After 5 days post-transfection, cells were harvested and analyzed on a FACS-Celesta machine (Becton Dickinson) for mCherry (561 nm laser excitation, 610/20 filter for detection) and GFP (488 nm laser excitation, 530/30 filter for detection) fluorescence. Cells expressing mCherry were gated and percent GFP calculation of the subset were calculated. All samples were performed in duplicates and percentage values were averaged. Standard deviation was used to calculate error bars. The TLR spacer sequence is 5'-TTCTGTAGTCGA-CGGTACCG-3' [SEQ ID No: 6].

Base Editing Evaluation Program. The Base Editing Evaluation Program (BEEP) was written in Python, employing the pandas data manipulation library and BioPython package. As inputs, the program requires a sample ab1 file, a negative control ab1 file, a target sequence, as well as the position of the specified base conversion, either handled as a .csv file for multiple sample analysis or for individual samples on the command line. Briefly, the provided target sequences are aligned to the base-calls of each input ab1 file to determine the absolute position of the target within the file. Subsequently, the peak values for each base at the indicated position in the spacer are obtained, and the editing percentage of the specified base conversion is calculated. Finally, a separate function normalizes the editing percentage to that of the negative control ab1 file to account for background signals of each base. The final base conversion percentage is outputted to the same .csv file for downstream analysis.

SPAMALOT Pipeline. All 11,440 Streptococcus bacterial and 53 Streptococcus associated phage genomes were downloaded from NCBI. CRISPR repeats catalogued for the genus were downloaded from CRISPRdb hosted by University of Paris-Sud [I. Grissa, G. Vergnaud, C. Pourcel, "The CRISPRdb database and tools to display CRISPRs and to generate dictionaries of spacers and repeats", BMC Bioinform. 8, 172 (2007)]. For each genome, spacers upstream of a specific repeat sequence were collected with a toolchain consisting of the fast and memory-efficient Bowtie 2 alignment [B. Langmead, S. L. Salzberg, "Fast gapped-read alignment with Bowtie 2", Nat. Methods 9, 357359 (2012)]. Each genome and repeat-type specific collection of spacers were then matched to all phage genomes using the original Bowtie short-sequence alignment tool [B. Langmead, C. Trapnell, M. Pop, S. L. Salzberg, "Ultrafast and memory-efficient alignment of short DNA sequences to the human genome", Genome Biol. 10, R25 (2009)] to identify candidate protospacers with at most one, two, or no mismatches. Unique candidates were input into the WebLogo 3 [Crooks, G. E. et al. "WebLogo: a sequence logo generator", Genome Res. 14, 1188-1190 (2004)] command line tool for prediction of PAM features.

Statistical analysis. Data are shown as mean±s.d., unless stated otherwise. Statistical analysis was performed using the two-tailed Students t-test, utilizing the SciPy software package. Calculated p-values, as compared to the negative control, are represented as follows: *P≤0.05, P≤0.01, *P≤0.001, and ****P≤0.0001. Data was plotted using Matplotlib.

At least the following aspects, implementations, modifications, and applications of the described technology are contemplated by the inventors and are considered to be aspects of the invention:

(1) An isolated *Streptococcus canis* Cas9 (ScCas9) protein or transgene expression thereof.

(2) Naturally-occurring and engineered CRISPR-associated DNA endonucleases with PAM interacting domain (PID) amino acid sequences that are at least 80% identical to that of the isolated *Streptococcus canis* Cas9 (ScCas9) protein.

(3) The isolated *Streptococcus canis* Cas9 (ScCas9) protein, comprising one or more of the following mutations: K857A, K1012A, R1069A, N507A, R671A, Q705A, Q935A, N702A, M704A, Q705A, H708A.

(4) CRISPR-associated DNA endonucleases with a PAM specificity of "NNGT" or "NNNGT".

(5) Naturally-occurring CRISPR-associated DNA endonucleases comprising a 10 amino acid loop insertion of "IKHRKRTTKL" [SEQ ID No: 4] and their associated PAM specificities.

(6) Naturally-occurring CRISPR-associated DNA endonucleases comprising a 2 amino acid insertion of "KQ" two positions upstream of the first critical arginine (R) residue for PAM binding and their associated PAM specificities.

(7) An isolated, engineered *Streptococcus pyogenes* Cas9 (SpCas9) protein with its PID as either the PID amino acid composition of the isolated *Streptococcus canis* Cas9 (ScCas9) protein or of CRISPR-associated DNA endonucleases with PAM interacting domain (PID) amino acid sequences that are at least 80% identical to that of the isolated *Streptococcus canis* Cas9 (ScCas9) protein.

(8) An isolated, engineered SpCas9 protein comprising one or both of the amino acid insertions of (5) and (6).

(9) An isolated, engineered *Streptococcus thermophilus* Cas9 (StCas9) protein comprising one or both of the amino acid insertions of (5) and (6).

(10) An isolated, engineered Cpf1 protein comprising one or both of the amino acid insertions of (5) and (6).

(11) A method of altering expression of at least one gene product comprising: introducing into a eukaryotic cell containing and expressing a DNA molecule having a target sequence and encoding the gene product, an engineered, non-naturally occurring Clustered Regularly Interspaced Short Palindromic Repeats (CRISPR)—CRISPR associated (Cas) (CRISPR-Cas) system comprising one or more vectors comprising (a) a regulatory element operable in a eukaryotic cell operably linked to at least one nucleotide sequence encoding a CRISPR system guide RNA that hybridizes with the target sequence, and (b) a second regulatory element operable in a eukaryotic cell operably linked to a nucleotide sequence encoding one or more of the proteins in (1)-(10), wherein components (a) and (b) are located on same or different vectors of the system, whereby the guide RNA targets the target sequence and one or more of the proteins in (1)-(10) cleave the DNA molecule, whereby expression of the at least one gene product is altered; and, wherein the proteins and the guide RNA do not naturally occur together.

The present invention demonstrates the natural PAM plasticity of a highly similar, yet previously uncharacterized, Cas9 from *Streptococcus canis* (ScCas9) through rational manipulation of distinguishing motif insertions. Affinity to minimal 5'-NNG-3' PAM sequences and the accurate editing capabilities of the ortholog in both bacterial and human cells have been demonstrated. In one aspect of the invention, an automated bioinformatics pipeline, the Search for PAMs by ALignment Of Targets (SPAMALOT) further explores the microbial PAM diversity of otherwise-overlooked *Streptococcus* Cas9 orthologs. The results establish that ScCas9 can be utilized both as an alternative genome editing tool and as a functional platform to discover novel *Streptococcus* PAM specificities.

While preferred embodiments of the invention are disclosed herein, many other implementations will occur to one of ordinary skill in the art and are all within the scope of the invention. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. Other arrangements, methods, modifications, and substitutions by one of ordinary skill in the art are therefore also considered to be within the scope of the present invention.

What is claimed is:

1. An isolated *Streptococcus canis* Cas9 (ScCas9) protein, modified to include at least one of the mutations K857A, K1012A, R1069A, N507A, R671A, Q705A, Q935A, N702A, M704A, Q705A, or H708A, or transgene expression thereof, in complex with a CRISPR system guide RNA that hybridizes with a target sequence, wherein the protein and the guide RNA do not naturally occur together, the protein and the guide RNA together forming an engineered, non-naturally occurring CRISPR-Cas system.

2. The protein of claim 1, wherein the protein comprises a CRISPR-associated DNA endonuclease with Protospacer Adjacent Motif (PAM) interacting domain (PID) amino acid sequences that are at least 80% identical to that of an isolated wild-type *Streptococcus canis* Cas9 (ScCas9) protein comprising SEQ ID NO: 8.

3. The protein of claim 2, having a PAM specificity of "NNGT" or "NNNGT".

4. The protein of claim 2, comprising a 10-amino acid loop insertion of "IKHRKRTTKL" [SEQ ID No: 4].

5. The protein of claim 2, comprising a 2-amino acid insertion of "KQ" two amino acid positions N-terminus of the first critical arginine (R) residue for PAM binding.

6. A method of altering expression of at least one gene product comprising:
   introducing into a eukaryotic cell containing and expressing a DNA molecule having a target sequence and encoding the gene product, an engineered, non-naturally occurring CRISPR-Cas system comprising one or more vectors comprising
   (a) a regulatory element operable in a eukaryotic cell operably linked to at least one nucleotide sequence encoding a CRISPR system guide RNA that hybridizes with the target sequence, and
   (b) a second regulatory element operable in a eukaryotic cell operably linked to a nucleotide sequence encoding one or more proteins selected from the group consisting of: (i) an isolated *Streptococcus canis* Cas9 (ScCas9) protein, modified to include at least one of the mutations K857A, K1012A, R1069A, N507A, R671A, Q705A, Q935A, N702A, M704A, Q705A, or H708A, and (ii) a CRISPR-associated DNA endonuclease with PAM interacting domain (PID) amino acid sequences that are at least 80% identical to that of the isolated wild-type *Streptococcus canis* Cas9 (ScCas9) protein comprising SEQ ID NO: 8, modified to include at least one of the mutations K857A, K1012A, R1069A, N507A, R671A, Q705A, Q935A, N702A, M704A, Q705A, or H708A, wherein components (a) and (b) are located on same or different vectors of the system, whereby the guide RNA targets the target sequence and one or more of the proteins cleave the DNA molecule, whereby expression of the at least one gene product is altered, and wherein the proteins and the guide RNA do not naturally occur together.

7. The method of claim 6, wherein protein (ii) of component (b) has a PAM specificity of "NNGT" or "NNNGT".

8. The method of claim 6, wherein protein (ii) of component (b) has a 10-amino acid loop insertion of "IKHRKRTTKL" [SEQ ID No: 4].

9. The method of claim 6, wherein protein (ii) of component (b) has a 2-amino acid insertion of "KQ" two amino acid positions N-terminus of the first critical arginine (R) residue for PAM binding.

* * * * *